United States Patent
Lish et al.

(10) Patent No.: US 12,232,783 B2
(45) Date of Patent: Feb. 25, 2025

(54) ROD REDUCTION ASSEMBLIES AND RELATED METHODS

(71) Applicant: NuVasive, Inc., San Diego, CA (US)

(72) Inventors: Scott Lish, Oceanside, CA (US);
Andrew Morris, San Diego, CA (US);
Niall Casey, Carlsbad, CA (US);
Robert German, San Diego, CA (US);
Jeffrey M. Seago, San Diego, CA (US);
Eugene Shoshtaev, Del Mar, CA (US)

(73) Assignee: Globus Medical Inc., Audubon, PA (US)

( * ) Notice: Subject to any disclaimer, the term of this patent is extended or adjusted under 35 U.S.C. 154(b) by 18 days.

(21) Appl. No.: 18/162,148

(22) Filed: Jan. 31, 2023

(65) Prior Publication Data

US 2023/0172644 A1 Jun. 8, 2023

Related U.S. Application Data

(63) Continuation of application No. 17/122,900, filed on Dec. 15, 2020, now Pat. No. 11,660,128, which is a continuation of application No. 16/201,884, filed on Nov. 27, 2018, now Pat. No. 10,898,241, which is a continuation of application No. 14/634,729, filed on Feb. 28, 2015, now Pat. No. 10,136,927, which is a continuation-in-part of application No. 14/217,101, filed on Mar. 17, 2014, now Pat. No. 9,486,256.

(60) Provisional application No. 61/802,046, filed on Mar. 15, 2013.

(51) Int. Cl.
*A61B 17/70* (2006.01)
*A61B 17/00* (2006.01)

(52) U.S. Cl.
CPC ...... *A61B 17/7086* (2013.01); *A61B 17/7083* (2013.01); *A61B 2017/00367* (2013.01); *A61B 2017/00407* (2013.01); *A61B 2017/00477* (2013.01)

(58) Field of Classification Search
CPC ........................................ A61B 17/7074–7092
See application file for complete search history.

(56) References Cited

U.S. PATENT DOCUMENTS

| | | | |
|---|---|---|---|
| 6,648,888 B1 * | 11/2003 | Shluzas | A61B 17/7086 606/86 A |
| 7,278,995 B2 * | 10/2007 | Nichols | A61B 17/7032 606/272 |
| 9,084,642 B2 * | 7/2015 | Peultier | A61B 17/7082 |
| 10,898,241 B2 * | 1/2021 | Lish | A61B 17/7083 |
| 2006/0089651 A1 * | 4/2006 | Trudeau | A61B 17/7086 606/86 R |
| 2007/0032162 A1 * | 2/2007 | Jackson | A61B 17/7082 446/1 |

(Continued)

*Primary Examiner* — Eduardo C Robert
*Assistant Examiner* — Steven J Cotroneo

(57) ABSTRACT

This disclosure describes example embodiments of rod reduction instrumentation and other rod and vertebrae manipulation instruments. The rod reducers can be used during the installation of a rod based surgical fixation system to help urge the rod into the fixation anchors. The reducers described provide various configurations delivering large reduction distance capabilities, strong controlled reduction coupled with an ability to quickly advance the reducer if desired, and reduction of bulk through the surgical corridor.

20 Claims, 19 Drawing Sheets

(56) References Cited

U.S. PATENT DOCUMENTS

| | | | |
|---|---|---|---|
| 2009/0157125 A1* | 6/2009 | Hoffman | A61B 17/7091 606/86 A |
| 2011/0202096 A1 | 8/2011 | White et al. | |
| 2013/0018419 A1* | 1/2013 | Rezach | A61B 17/7076 606/264 |
| 2013/0090697 A1* | 4/2013 | George | A61B 17/7091 606/305 |
| 2014/0148865 A1* | 5/2014 | Hennard | A61B 17/7086 606/86 A |

* cited by examiner

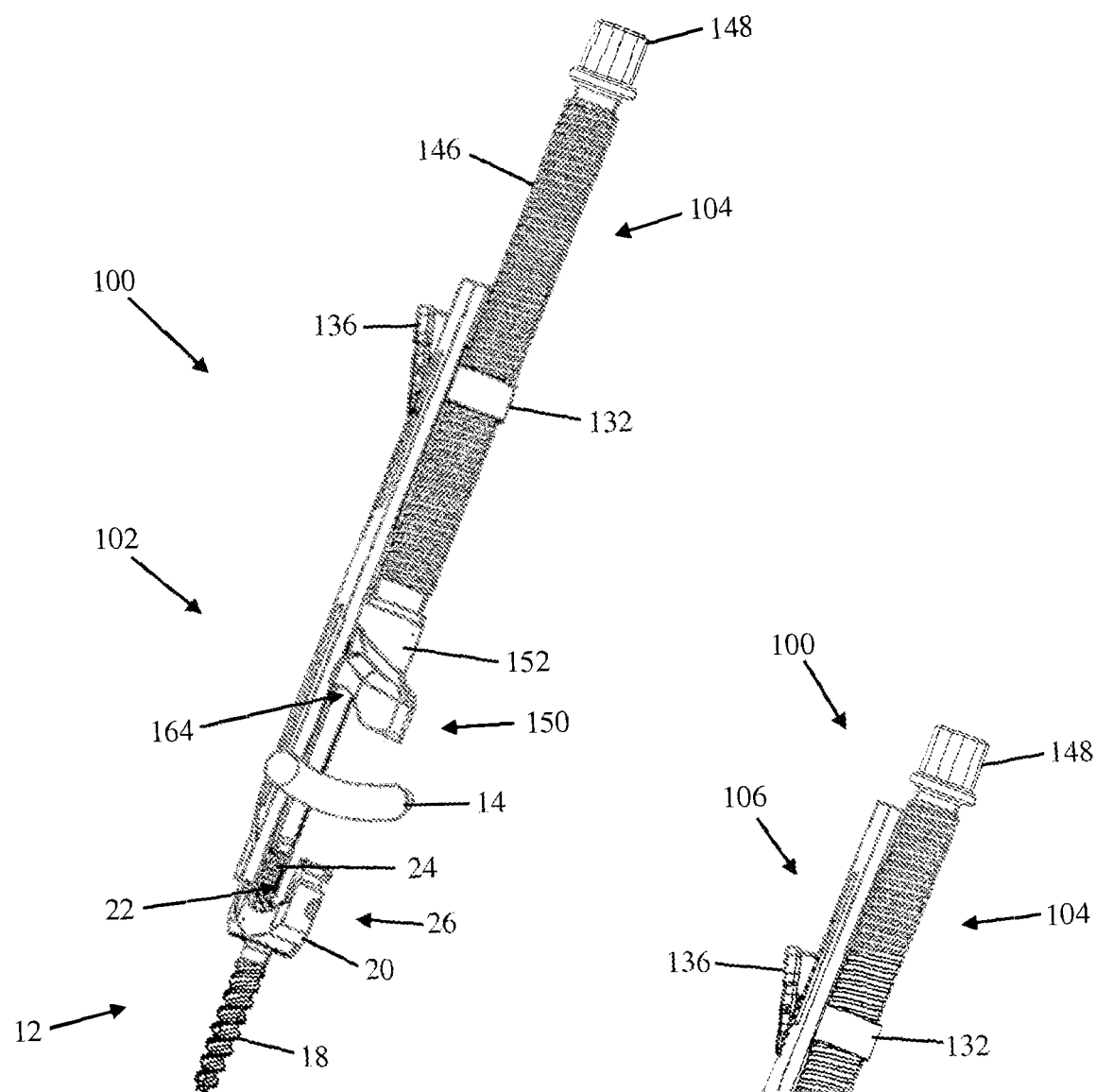
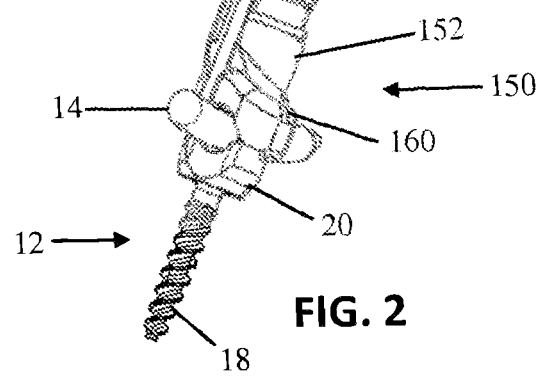
FIG. 1
FIG. 2

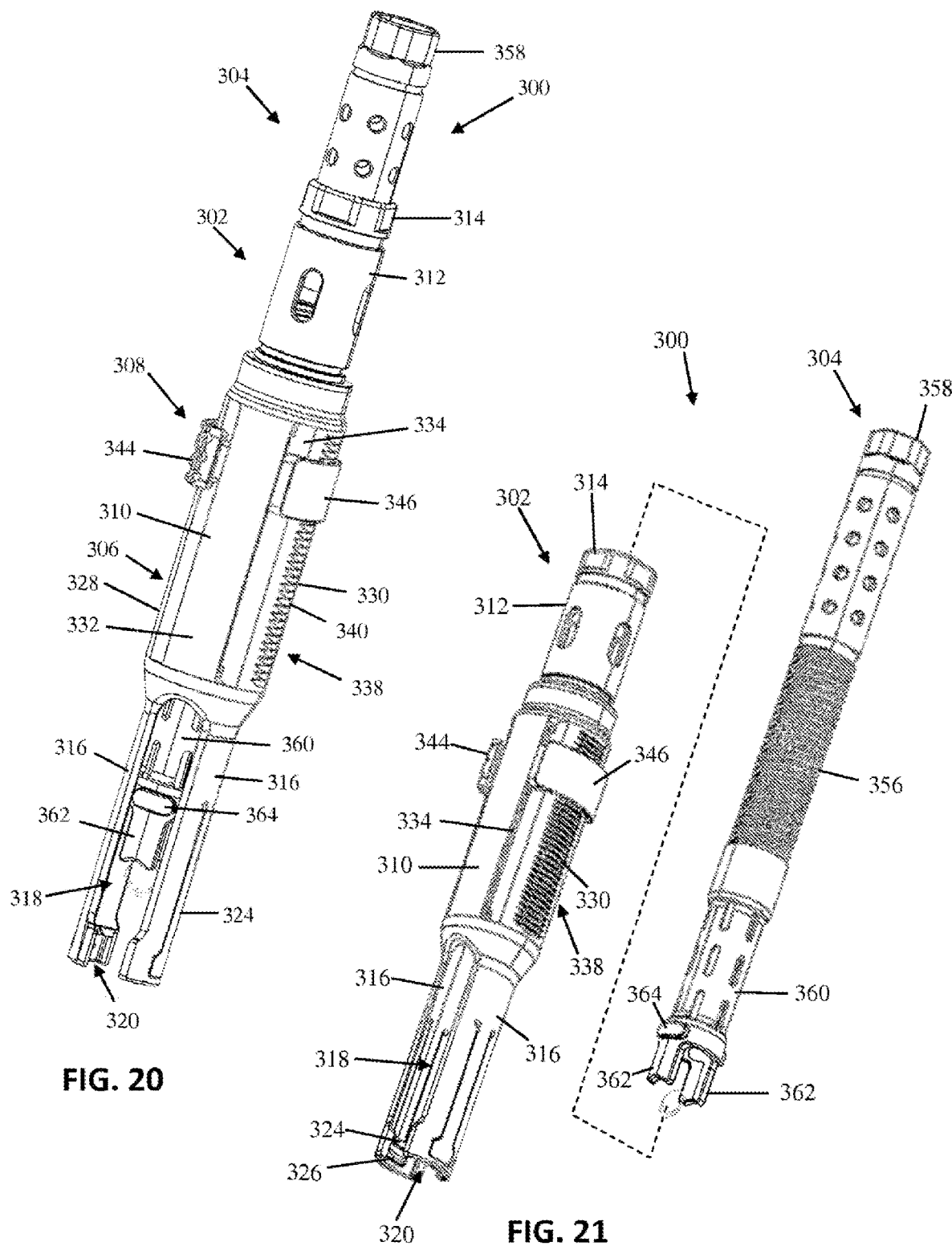

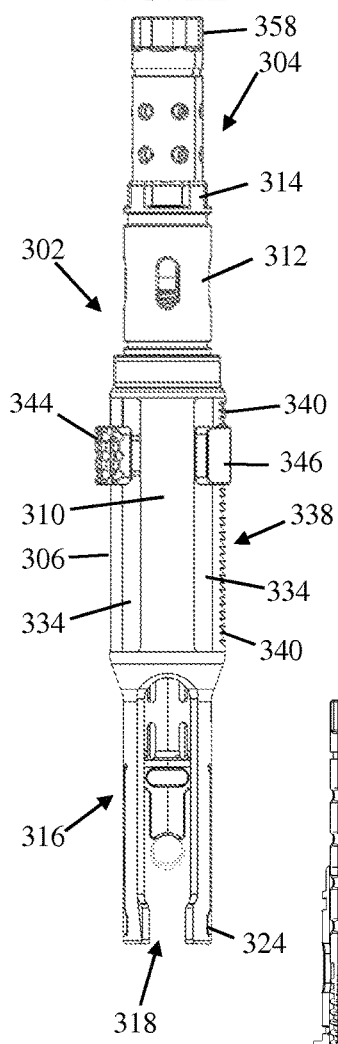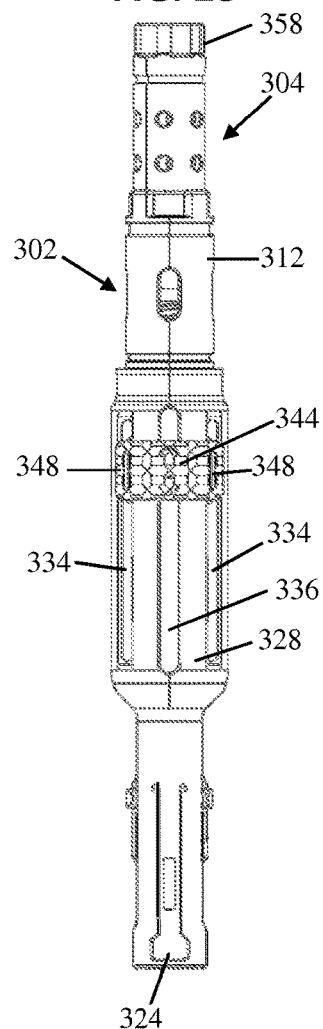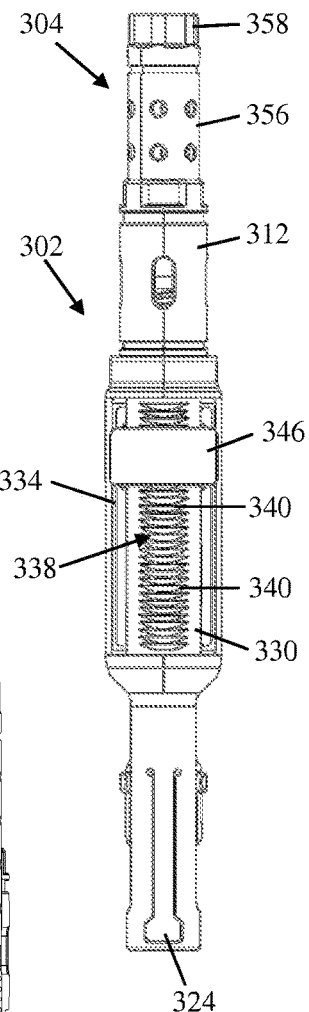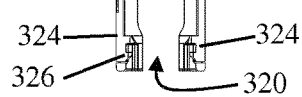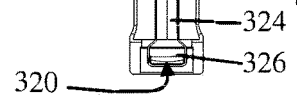

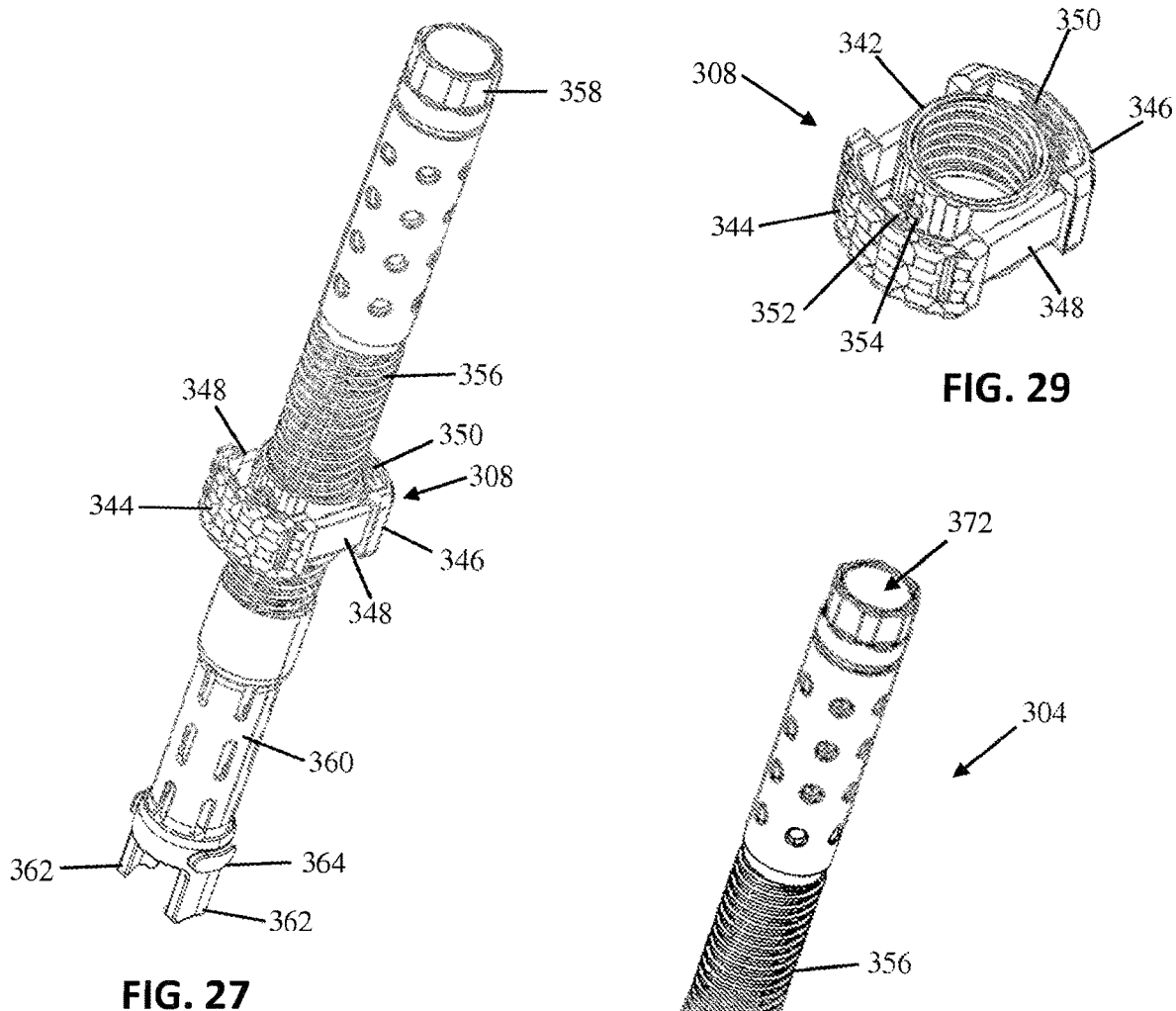

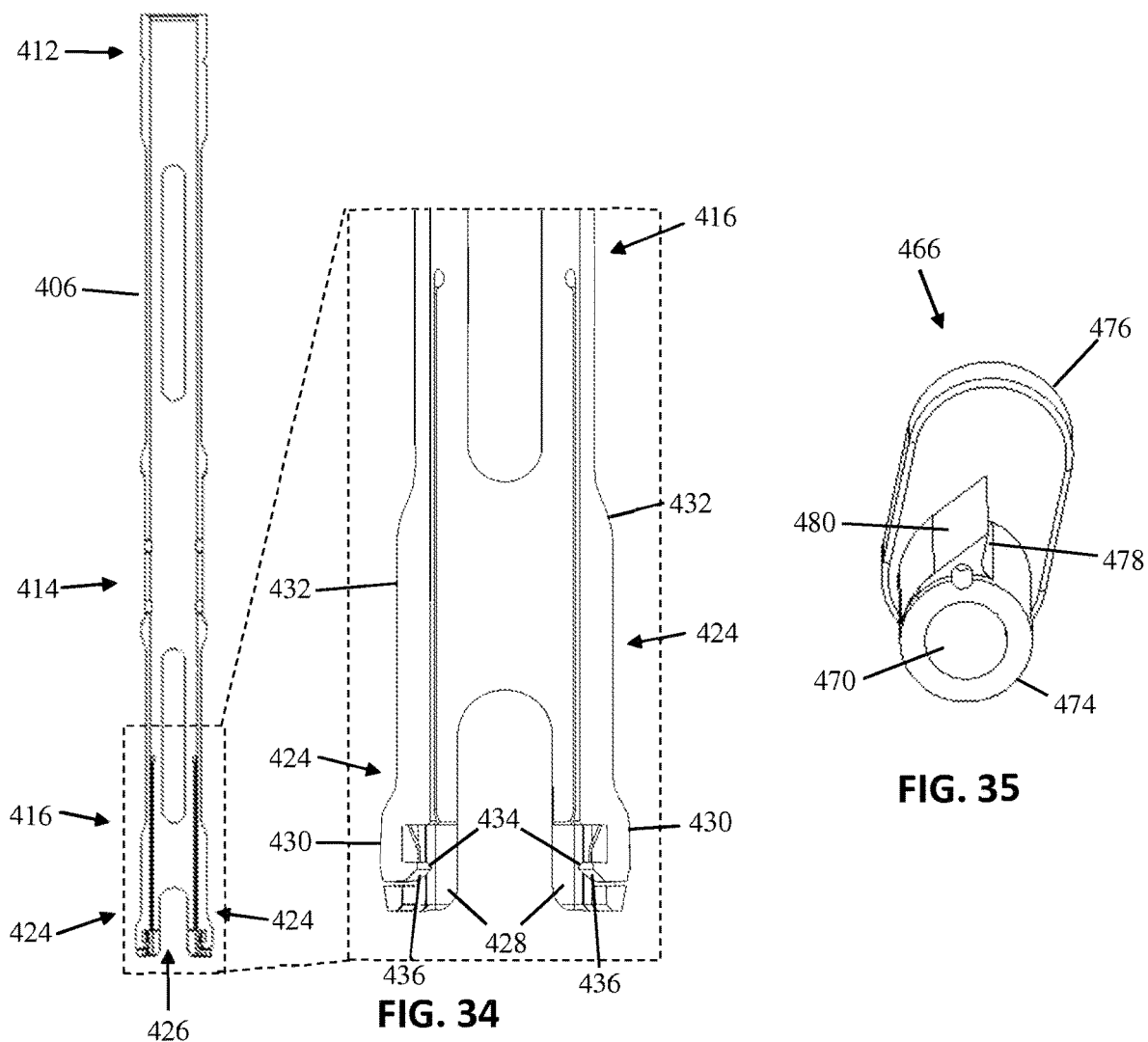
FIG. 35
FIG. 34
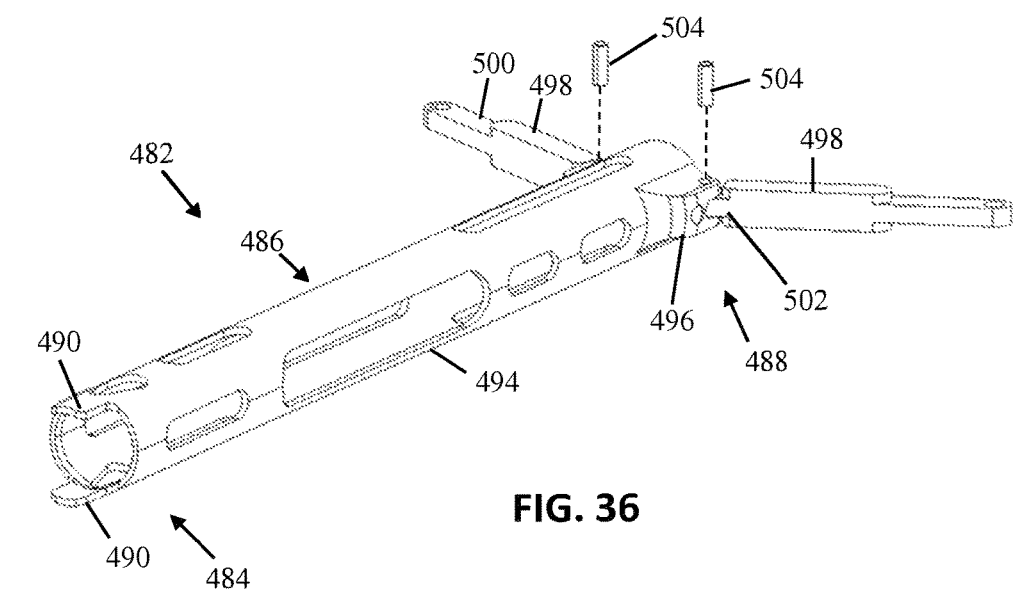
FIG. 36

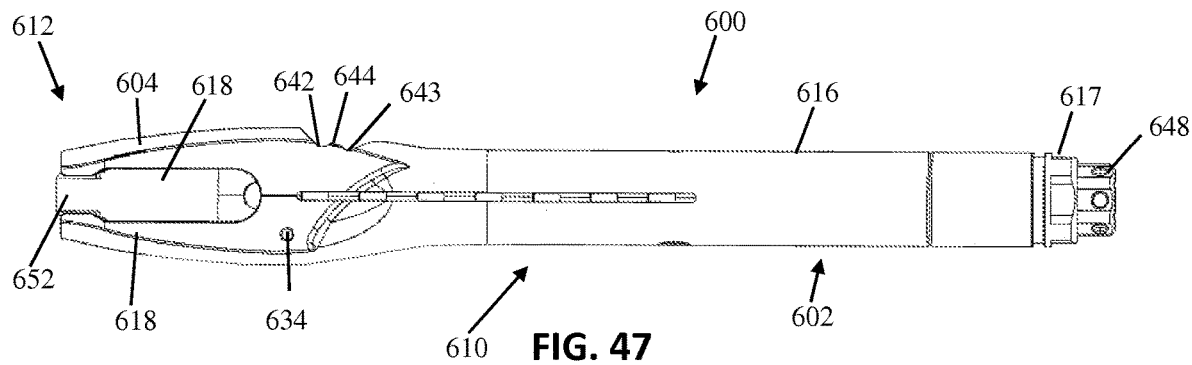
FIG. 47
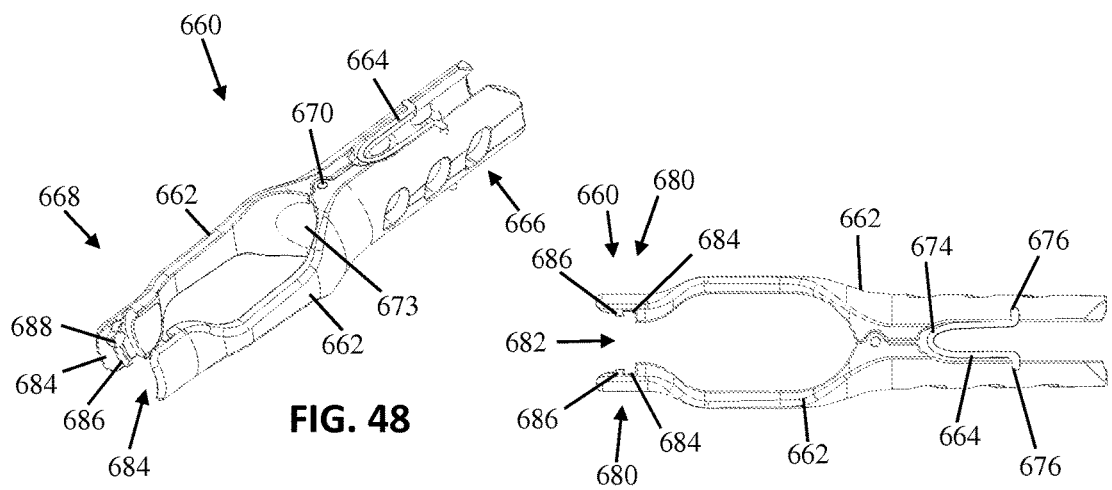
FIG. 48
FIG. 49
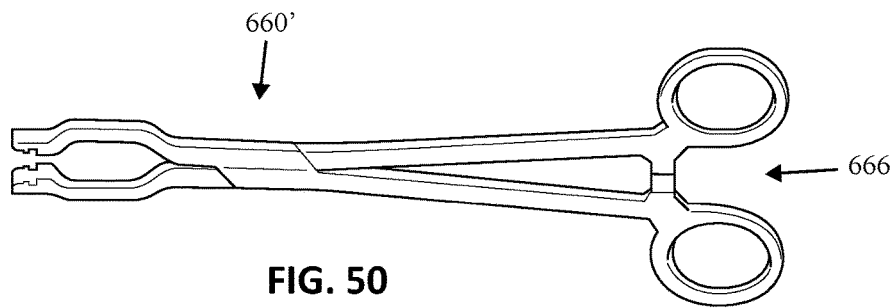
FIG. 50

ROD REDUCTION ASSEMBLIES AND RELATED METHODS

CROSS-REFERENCE TO RELATED APPLICATIONS

The present application is a continuation of U.S. patent application Ser. No. 17/122,900, filed on Dec. 15, 2020, which is a continuation of U.S. patent application Ser. No. 16/201,884 (now U.S. Pat. No. 10,898,241), filed on Nov. 27, 2018, which is a continuation of U.S. patent application Ser. No. 14/634,729 (now U.S. Pat. No. 10,136,927) filed on Feb. 28, 2015, which is a continuation-in-part of U.S. patent application Ser. No. 14/217,101 (now U.S. Pat. No. 9,486,256), filed on Mar. 17, 2014, which claims priority to U.S. Provisional Patent Application No. 61/802,046, filed on Mar. 15, 2013, the entire contents of which are hereby expressly incorporated by reference into this disclosure as if set forth fully herein.

FIELD

The present application relates to the field of spinal surgery and spinal fixation devices, including instruments and associated methods for seating or reducing a spinal fixation rod into a fixation anchor during the installation of a spinal fixation construct.

BACKGROUND

Spinal fixation constructs are utilized to provide stability to the spine. Most often the fixation construct is used as an adjunct to fusion surgery during which adjacent vertebrae are prepared to facilitate bone growth between them. Because motion between the vertebrae tends to inhibit bone growth, the fixation constructs are employed to prevent motion so that bone can grow and achieve a solid fusion. When the position of one or more vertebrae must be adjusted to restore a more natural alignment of the spinal column, the fixation construct also serves to maintain the new alignment until fusion is achieved.

Fixation constructs of various forms are known in the art, of which, rod based fixation constructs are one of the most common. Typically in a rod based construct multiple anchors are coupled to a portion (e.g. the posterior elements) of two or more vertebrae and then connected by a fixation rod. The anchors further include a rod housing in which the fixation rod is captured and locked. The rod housing may be fixed or rotatably coupled to the anchor portion and generally includes a pair of upstanding arms separated by a rod channel. When constructing the fixation construct the surgeon must align and seat the rod in the rod channel of each anchor, an undertaking that is generally referred to as "reduction". Reduction can be a challenge, particularly when one or more of the vertebrae to be connected are out of alignment with other vertebrae, and the reduction distance and force requirements can vary greatly from anchor to anchor. Known rod reduction instruments or reducers, can be bulky, time consuming or frustrating to employ, limited in achievable reduction depth, and other issues that can make them less than desirable. The various rod reduction and other instruments described herein are directed towards facilitating simple and efficient rod and/or screw manipulation during installation of a fixation construct.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 1 is a perspective view of a rod reducer for urging a spinal rod to an anchor, according to a first example embodiment;

FIG. 2 is a perspective of the example rod reducer of FIG. 1 with the rod in a fully reduced position within the anchor;

FIG. 20 is a perspective view of a rod reducer according to a third example embodiment;

FIG. 21 is an exploded view illustrating the coupling unit and translation unit of the example reducer of FIG. 20;

FIG. 22 is a side view of the example rod reducer of FIG. 20;

FIG. 23 is a front side view of the example rod reducer of FIG. 20;

FIG. 24 is a backside view of the example rod reducer of FIG. 20;

FIG. 25 is a cross-section view of the example rod reducer of FIG. 20 viewed in FIG. 22;

FIG. 26 is a cross-section view of the example rod reducer of FIG. 20 as viewed in FIG. 24;

FIG. 27 is a perspective view of a translating unit and translating coupler of the example rod reducer of FIG. 20;

FIG. 28 is a perspective view of the translating unit of FIG. 27;

FIG. 29 is a perspective view of the translating coupler of FIG. 27;

FIG. 34 is a sectional plan view of a base member forming part of the coupling unit of FIG. 33;

FIG. 35 is a perspective view of a ratchet post forming part of the coupling unit of FIG. 33;

FIG. 36 is a perspective view of a translation unit forming part of the example rod reducer of FIG. 31;

FIG. 47 is a side view of the rod reducer of FIG. 44 with a lever arm removed for illustrative purposes;

FIG. 48 is a perspective view of an anchor clip according to an example embodiment;

FIG. 49 is a plan view of the anchor clip of FIG. 49;

FIG. 50 is a plan view of another example embodiment of an anchor clip;

DETAILED DESCRIPTION

Figure 3:
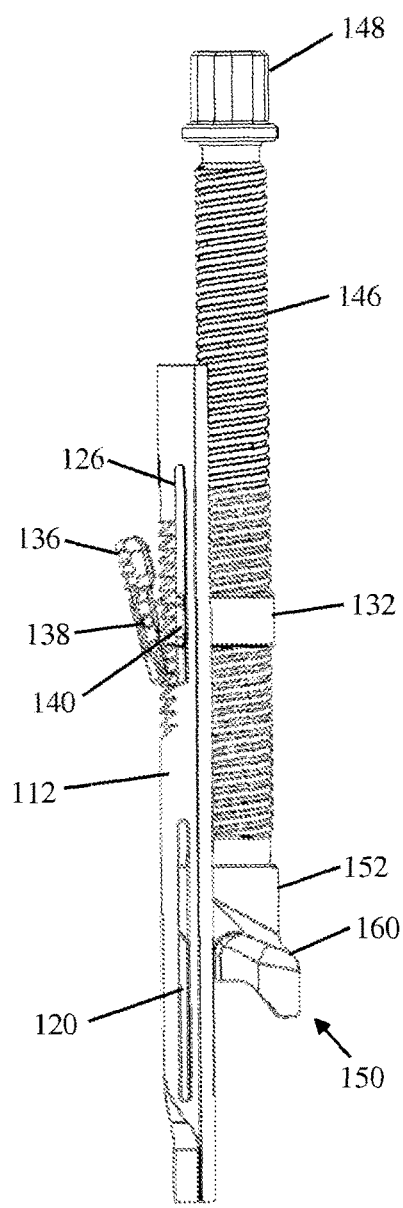
FIG. 3 is a side view of the example rod reducer of FIG. 1.
Figure 4:
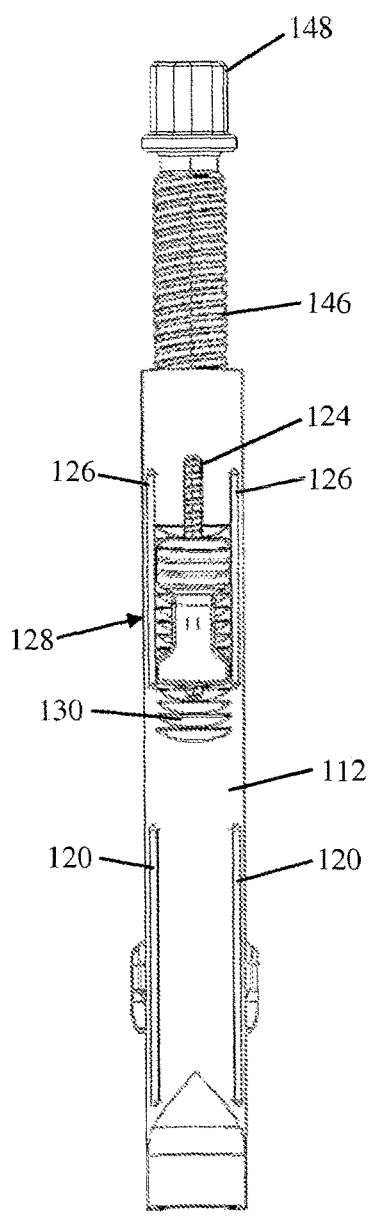
FIG. 4 is a backside view of the example rod reducer of FIG. 1.
Figure 5:
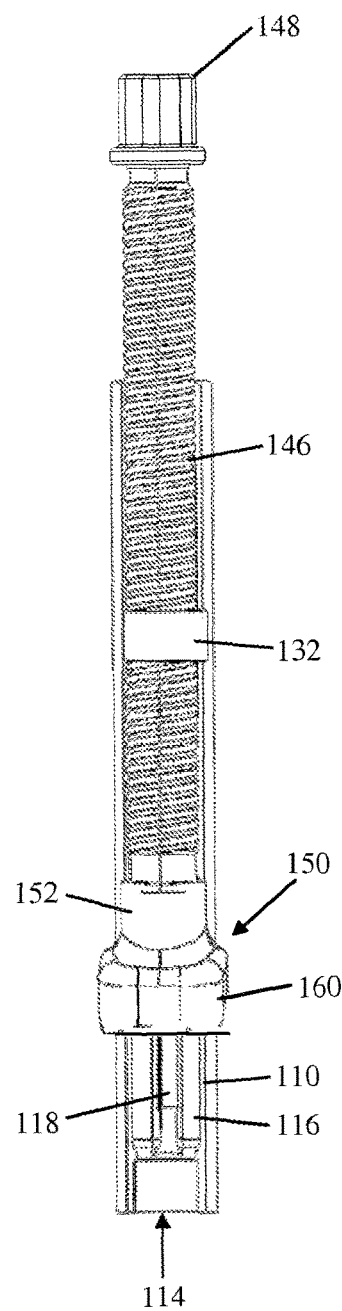
FIG. 5 is a front side view of the example rod reducer of FIG. 1.

Various example embodiments of devices and techniques for rod reduction during spinal instrumentation procedures are described herein. In the interest of clarity, not all features of an actual implementation are necessarily described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The rod reduction instruments and related implants, instruments and methods described herein boast a variety of inventive features and components that warrant patent protection, both individually and in combination.

The example reduction assembly, or reducer, embodiments described herein are used during the installation of a fixation construct 10 onto the spine of a patient. The fixation construct 10 includes anchor members 12 connected by a fixation rod 14 locked to each anchor 12. An anchor 12 is implanted in each vertebra to be fixed by the construct 10. For example, two anchors 12 may be used to fix two vertebrae together; three may be used to fix three vertebrae together; four may be used to fix four vertebrae together; and so on. The anchor 12 includes a bone anchor 18 and a housing 20 for capturing and locking a fixation rod 14. The bone anchor 18 may be a bone screw suitable for stable fixation to vertebral bone (e.g. pedicle or vertebral body), as shown. The bone anchor 18 may also include other fixation devices (e.g. hooks, staples, clamps, etc.). The housing 20 has a base that attaches with the bone anchor and a pair of upstanding arms that together form a rod channel 22. The housing also includes a mechanism 24 to lock the fixation rod 14 in position in the rod channel 22. For example, the mechanism 24 may include a locking cap guide and advancement feature disposed on the interior face of each arm that interacts with a complementary feature on a locking cap 16. The base may be fixed to the anchor 18 or may be coupled such that the housing can rotate in one or more directions (e.g. polyaxially). The housing also includes one or more instrument engagement features 26 for releasably coupling to one or more instruments during implantation. One example of an anchor configured for use with the reducers described herein is shown and described in U.S. patent application Ser. No. 13/456,210, filed Apr. 25, 2012, the entire contents of which are incorporated herein by reference. The reducers described herein can be engaged to one or more of the anchors 12 of the fixation construct 10 to facilitate alignment and advancement of the rod 14 into the rod channel 22 of each anchor.

Figure 18:
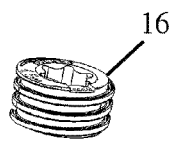
FIG. 18 is a perspective view of an example embodiment of a locking cap for use with the reducers of FIGS. 1, 13, and 20.
Figure 19:
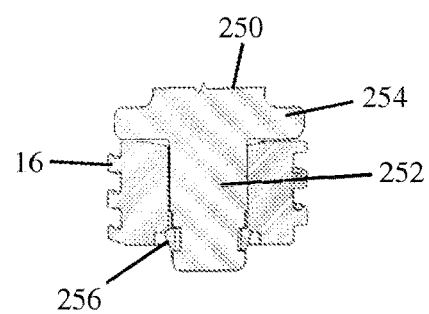
FIG. 19 is a cross-section view of the example locking cap of FIG. 18 preloaded onto the reducer of FIG. 13, according to one example embodiment.

With reference to FIGS. 1-12, a reducer 100 according to a first example embodiment is illustrated. As depicted in FIG. 1 the reducer 100 is configured to couple to a single side or arm of anchor 12 (advantageously reducing bulk in the surgical corridor) and impart a downward force on the rod 14. The downward force on the rod acts to draw the rod and anchor housing 20 together until the rod 14 fully seats in the rod channel 22, as shown in FIG. 2. A locking mechanism, such as locking cap 16 (see FIG. 18), may then be at least partially engaged to capture the rod 14 in the housing 20 prior to decoupling the reducer 100 from the anchor 12. The reducer 100 includes a coupling unit 102 that connects to the anchor 12 and a translation unit 104 that translates relative to the coupling unit 102 to urge the rod 14 towards the anchor.

Figure 6:
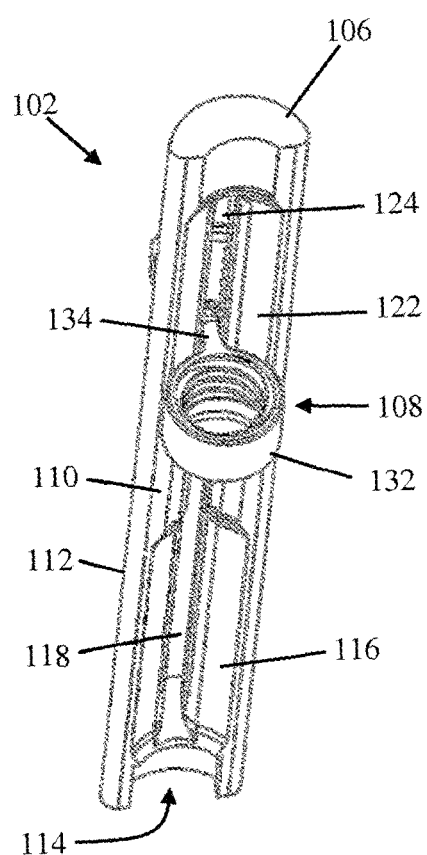
FIG. 6 is a perspective view of a coupling unit of the example rod reducer of FIG. 1.

With reference to FIG. 6, the coupling unit 102 includes a single anchor coupling arm 106 and a translation coupler 108. The anchor coupling arm 106 has a partially cylindrical profile with an inner face 110 and outer face 112. A cavity 114 at the distal end of the coupling arm 106 is dimensioned to snugly receive an arm of the anchor housing 20 therein. Included in the cavity is an engagement feature (not shown) that mates with the instrument engagement features 26 on the anchor to releasably fix the anchor housing 20 to the coupling arm 106. By way of example, the engagement feature may be the same or similar to the engagement feature 216 of reducer 200 described below. Above the cavity 114, the inner face 110 has a lower elongated concave recess 116 with a central slot 118 extending deeper still towards the outer face 112. A lower slot 120 generally coinciding with the length of the recess 116 extends through the coupling arm 106, opening near each edge of the outer face 112 and intersecting the central slot 118. The inner face 110 also includes an upper elongated concave recess 122 with a central slot 124 opening through the outer face. An upper slot 126 generally coinciding with the length of the recess 122 extends through the coupling arm 106, opening near each edge of the outer face 112 and intersecting the central slot 124. The outer face 112 includes a ridge track 128, having a series of downward pointing ridges 130. That is, the ridges 130 have an upper surface that slopes aggressively away and down from the outer face 112. The lower surface of ridges 130 may be perpendicular to the outer face, or preferably, may slope mildly also away and down from the outer face 112.

Figure 9:
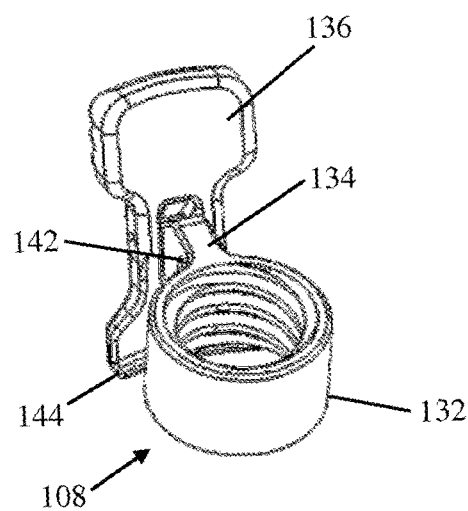
FIG. 9 is a perspective view of a translating coupler of the coupling unit of FIG. 6.

The translation coupler 108, shown in FIG. 9, includes an internally threaded ring 132. A wing 134 extends from the ring 132 through the central slot 124 and is pivotally connected to a switch 136 via pin 138 or other suitable mechanism. A stabilizing bar 140 situated in slot 126 passes through an aperture 142 in the wing 134 to fix the translation coupler 108 to the coupling arm 106 while allowing the translation coupler to translate up and down along the slot 126 and upper recess 122. A pawl 144 at the distal end of the switch 136 engages the ridge track 128 to prevent upward or proximal translation without disengaging the pawl 144. In a preferred example, the switch 136 is spring biased to the engaged pivot position. In this configuration, the application of downward force causes the pawl 144 to slide down the slope of the upper surface of each ridge 130 and automatically return to the engaged position when the pawl 144 passes the lower surface of the ridge 130. Thus, the translation coupler 108 can be advanced distally without manipulating the switch 136 but requires a user to manipulate the switch 136 to disengage the pawl 144 and allow proximal translation.

Figure 7:
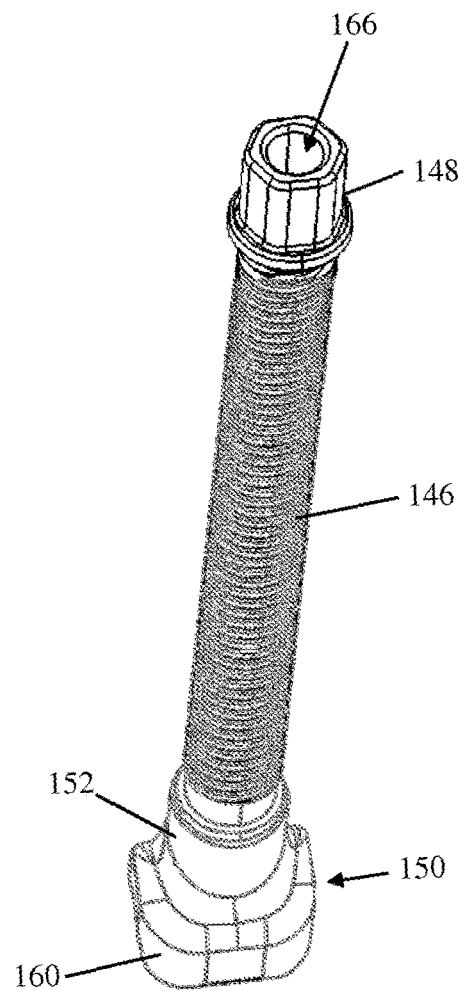
FIG. 7 is a perspective view of a translating unit of the example rod reducer of FIG. 1.
Figure 8:
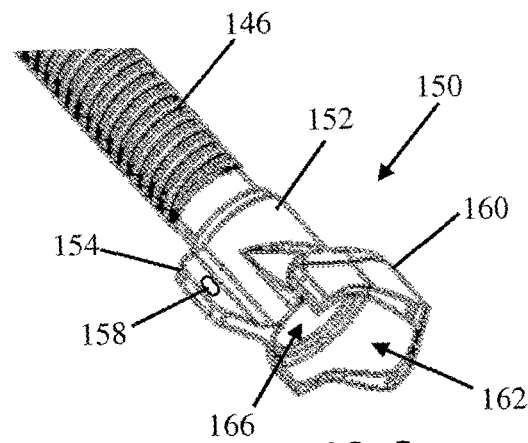
FIG. 8 is another perspective view of the distal end of the translating unit of FIG. 7.

With reference to FIGS. 7-8, the translation unit 104 includes a threaded shaft 146 capped with a drive nut 148 at the proximal end and a foot 150 configured to engage and drive the rod 14 at the distal end. The threaded shaft 146 engages the internal threading of the ring 132 to translate the translation unit 104 relative to the coupling unit 102 upon rotation of the shaft 146. The drive nut 148 can be engaged by a handle (not shown) to facilitate rotation. The foot 150 includes a cylindrical body 152 that complements the lower recess 116 and that is coupled to the shaft 146 in such a way that the foot 150 and shaft 146 are fixed longitudinally but freely rotatable relative to each other. This can be accomplished, for example, with an expansion ring situated in complementary internal and external grooves in the cylindrical body 152 and shaft 146, respectively. Or in one alternative, the distal end of the shaft 146 can include flexible fingers having a ridge that is received in the internal groove of the cylindrical body 152. A wing 154 extends from the cylindrical body and is situated in the central slot 118. A stabilizing bar 156 situated in slot 120 passes through an aperture 158 in the wing 154 to stabilize the foot and eliminate any movement of the foot other than translation up and down along the slot 120 and lower recess 116. A brim 160 extends out and down from the portion of the cylindrical body 152 not in contact with the inner recess 116. An inner cavity 162 enclosed by the brim 160 is configured to receive a portion of the anchor housing 20 therein. The front of brim 160 descends lower than the sides such that a rod recess 164 is formed between the coupling arm 102 and the brim front to help capture and guide the rod into the rod channel 22. Passage 166 extends through the translation unit 104 from the drive nut 148 to the foot 150 to receive locking cap 16 and a driver therethrough to engage the locking cap 16 to the housing 20 prior to removing the reducer 100. The translation unit 104 may further be configured to carry a preloaded locking cap, as illustrated below with respect to reducer 200.

Figure 10A:
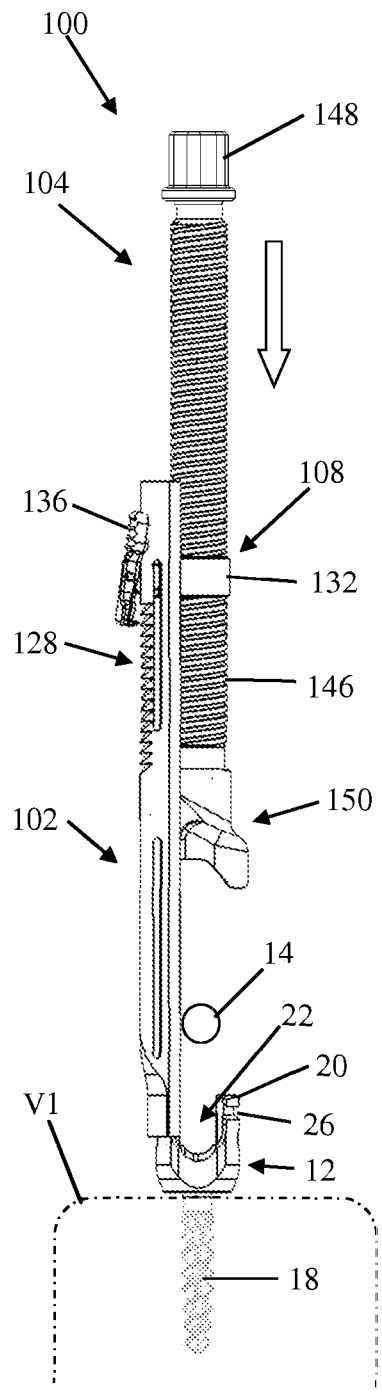
FIGS. 10A-10C are side views of the example reducer of FIG. 1 depicting a sequence for reducing a rod, according to one example embodiment.
Figure 10B:
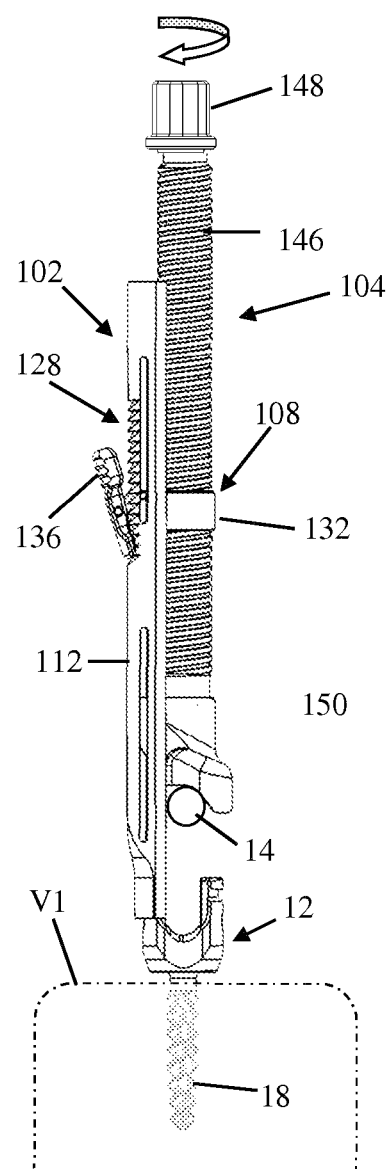
Figure 10C:
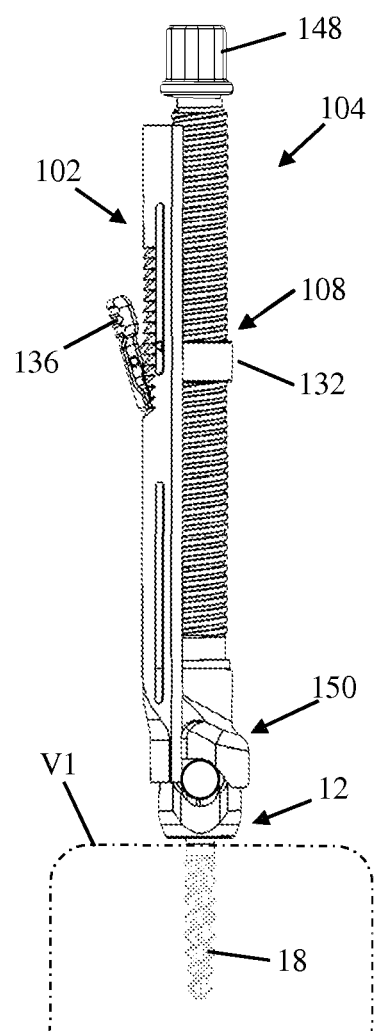
Figures 11, 12:
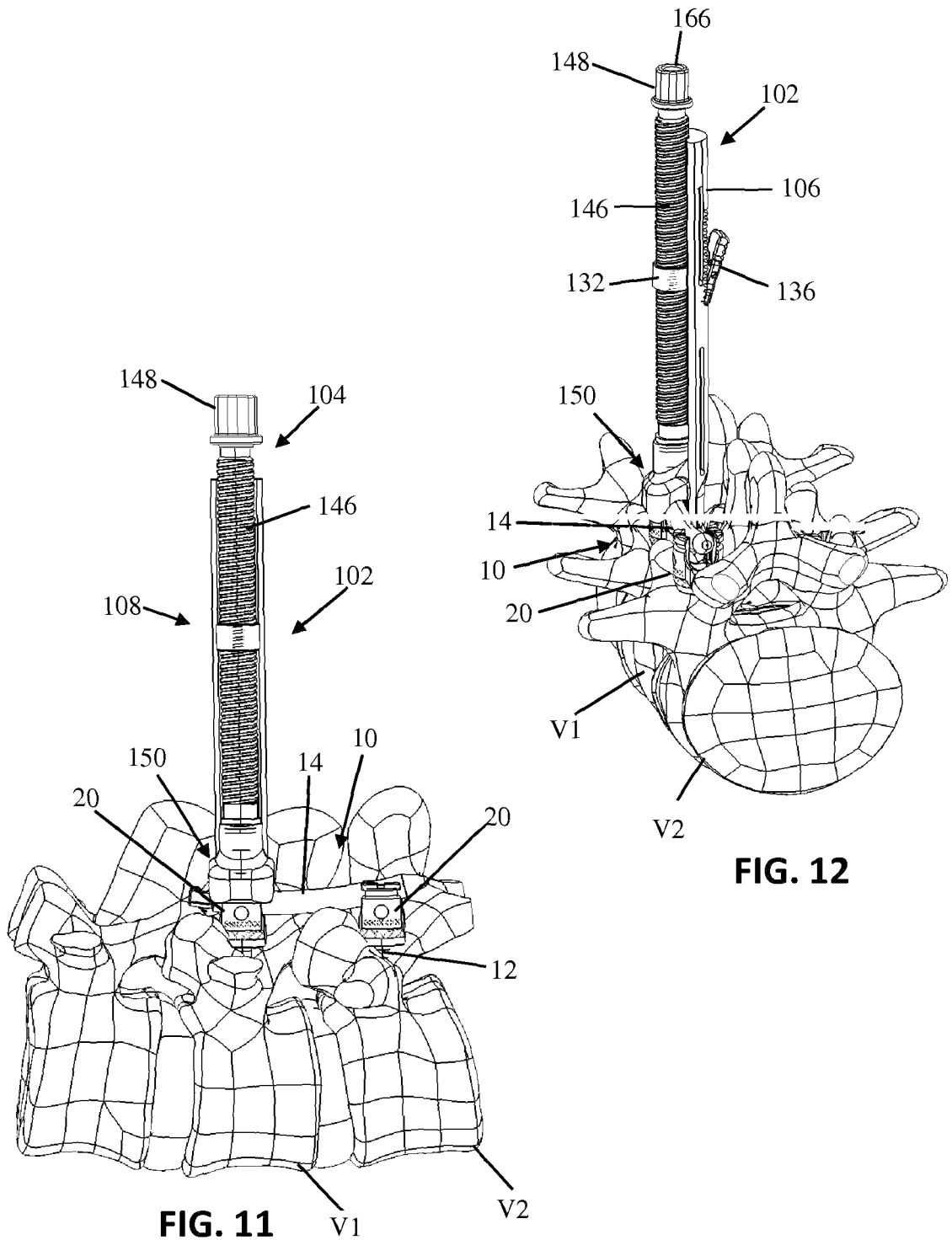
FIGS. 11-12 are lateral and perspective views illustrating the final reduction position shown in FIG. 10C in connection with a whole fixation construct fixing two adjacent vertebrae.
Figure 13:
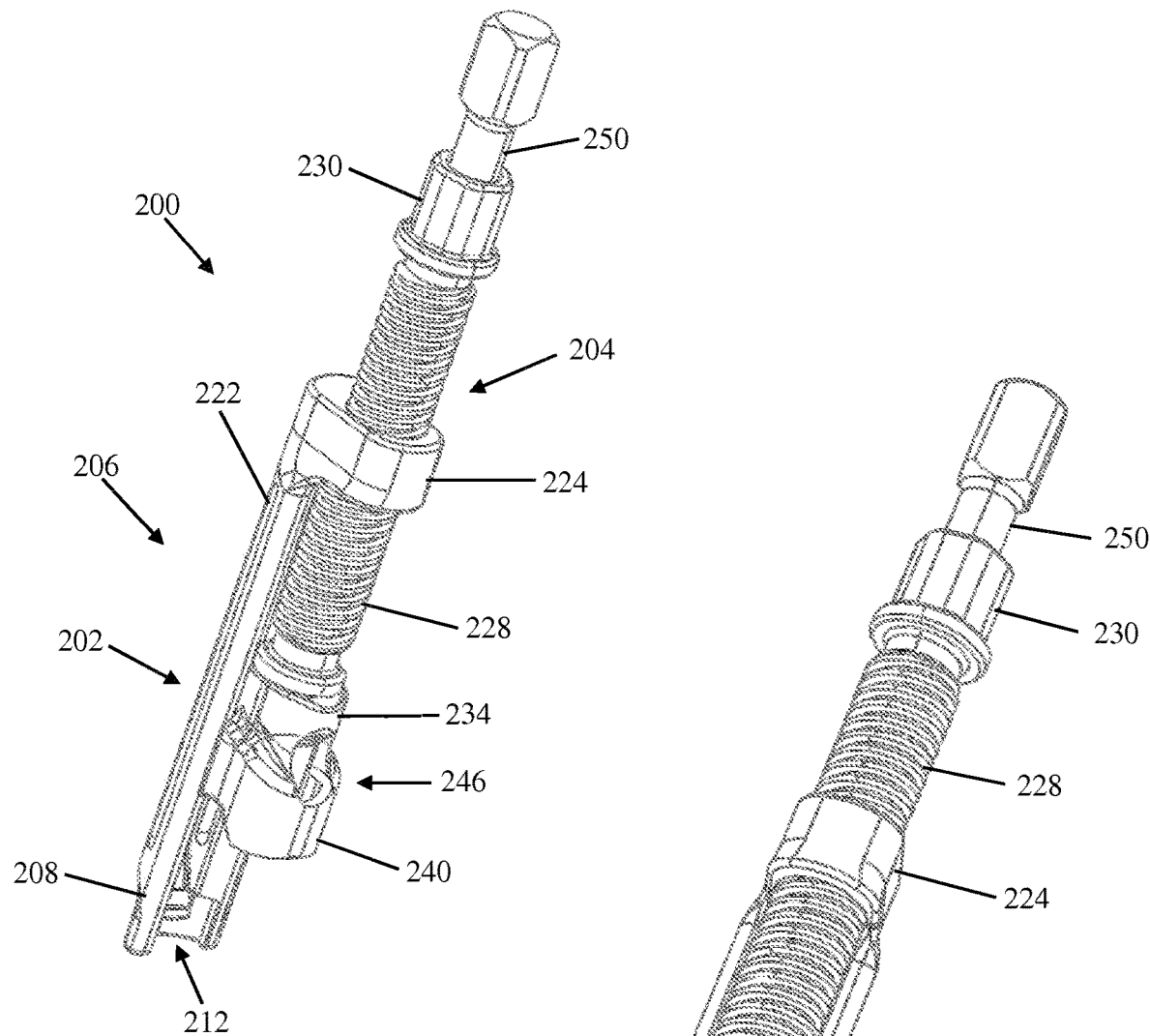
FIG. 13 is a perspective view of a rod reducer according to a second example embodiment.
Figure 14:
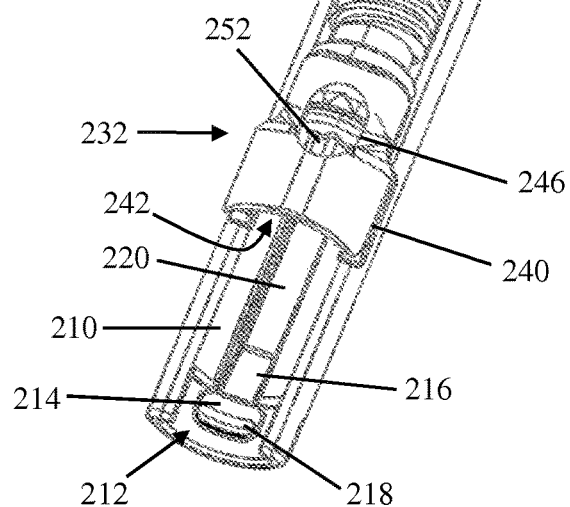
FIG. 14 is a different perspective view of the rod reducer of FIG. 13.
Figure 15:
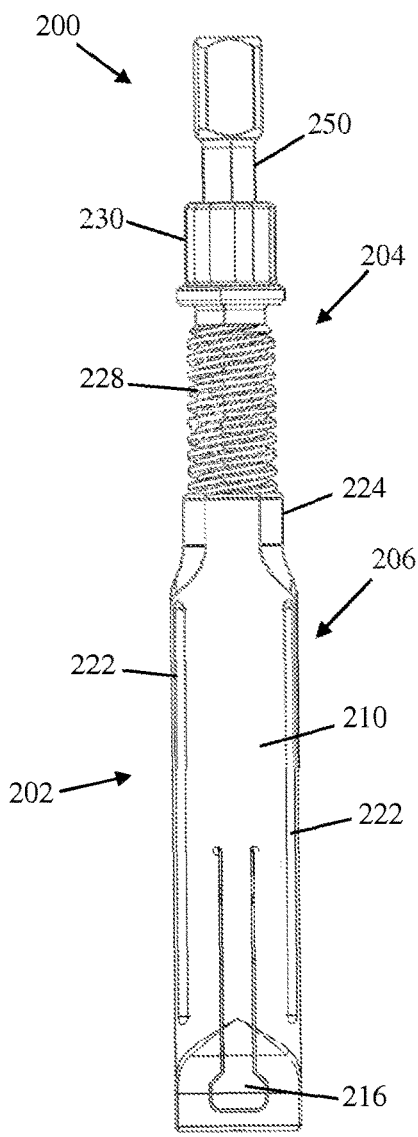
FIG. 15 is a back view of the example rod reducer of FIG. 13.
Figure 16:
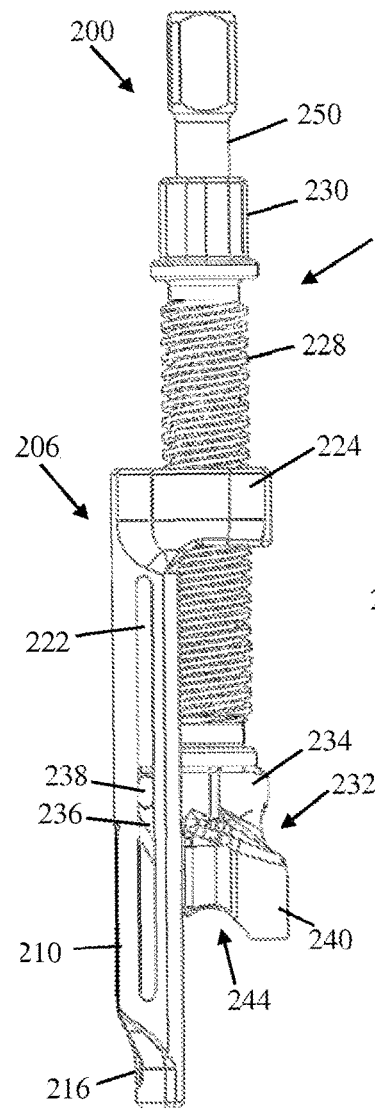
FIG. 16 is a side view of the example rod reducer of FIG. 13.

Turning to FIGS. 10A-10C, use of the reducer 100 is illustrated by way of example. Anchors 12 are implanted in each of the vertebra to be fixed, including anchor 12 in vertebra V 1 which is the anchor to be reduced in this example, and the rod is inserted to the anchor housings. As seen in FIG. 10A, the rod rests above the housing 20. The distal end of the coupling arm 102 is advanced onto an arm of the anchor housing 20 until the engagement features on the coupling arm 102 engage with the engagement feature 26 of the housing 20. The coupling arm 102 is coupled to the housing with the foot 150 of the translation unit 104 spaced proximal to the housing 20 and the rod 14. The user can then direct force distally onto the translation unit 102 such that the translation coupler 108 translates distally along the coupling arm 102 (translating the translating unit 104 distally along with it). Thus, the translation coupler 108 acts as quick-advance mechanism to advance the translation unit 104 without requiring the added effort and time required to threadingly advance the shaft 146 through the threaded ring 132. As the translation coupler 108 and translation unit 104 are advanced, the pawl 144 engages each ridge 130 on the track 128 in turn to prevent unwanted proximal translation. The translation coupler 108 and translation unit 104 can be advanced this way until the translation unit bottoms out on the slots 124 and/or 126, the foot 150 reaches the rod 14 (FIG. 10B), or beyond that, the force required to further move the rod becomes too great. With the foot 150 in contact with the rod 14, the threaded shaft 146 is rotated to advance the threading through the threaded ring 132 until the rod is fully seated in the anchor housing 20, as shown in FIG. 10C. FIGS. 11 and 12 illustrate this final position shown in 10 C with the additional anchor 12 of fixation construct 10 implanted in adjacent vertebra V 2. Though shown as a two level construct, additional anchors 12 can be implanted in additional vertebrae to extend the construct 10 over multiple levels. The construct 10 may also be implanted bilaterally with additional anchors 12 and another rod 14 implanted on the contralateral side of the vertebrae V 1 and V 2. The reducer 100 may be used on any or all of the anchors 12 in the construct. After the rod 14 is fully seated in housing 20 a locking cap 16 can be advanced through the passage 166 and engaged with the locking engagement feature 24 to capture and lock the rod 14 to the anchor 12. The switch 136 can then be manipulated to disengage the pawl 144 from the track 128 retract the translating unit 104 if desired, and the coupling arm 102 is disengaged from the housing 20.

Turning to FIGS. 13-19, a reducer 200 according to a second example embodiment is illustrated. Reducer 200 is similar to reducer 100 and is also configured to couple to a single side or arm of anchor 12. The reducer 200 includes a coupling unit 202 that connects to the anchor 12 and a translation unit 204 that translates relative to the coupling unit 202 to urge the rod 14 towards the anchor. The coupling unit 202 includes a single anchor coupling arm 206. The anchor coupling arm 206 has a partially cylindrical profile with an inner face 208 and an outer face 210. A cavity 212 at the distal end of the coupling arm 206 is dimensioned to snugly receive an arm of the anchor housing 20 therein. An engagement feature 214 includes a flexible finger 216 formed in the coupling arm and having a distal ridge 218 that projects into the cavity 14 to engage the engagement features 26 of the housing 20. The distal surface of the ridge 218 is tapered to automatically deflect the finger 216 outward as the arm of housing 20 is advanced into cavity 212, permitting the ridge 218 to pass the top of the housing until it engages the feature 26. The inner face 208 includes a central slot 220 and a slot 222 that extends through the coupling arm 206 opening near each edge of the outer face 210 and intersecting the central slot 220. A fixed coupling body 224 projects inward from the proximal end of the coupling arm 206 and encloses a threaded passage 226.

The translation unit 204 includes a threaded shaft 228 capped with a drive nut 230 at the proximal end and a foot 232 configured to engage and drive the rod 14 at the distal end. The threaded shaft 228 engages the internal threading of the passage 226. The drive nut 230 can be engaged by a handle (not shown) to facilitate rotation that translates the translation unit 204 relative to the coupling unit 202. The foot 232 includes a generally cylindrical body 234 that complements the inner face 208 and that is coupled to the shaft 228 in such a way that the foot 232 and shaft 228 are fixed translationally but freely rotatable relative to each other. This can be accomplished, for example, with an expansion ring 237 situated in complementary internal and external grooves in the cylindrical body 234 and shaft 228, respectively. Or in one alternative example, the distal end of the shaft 228 can include flexible fingers having a ridge that is received in the internal groove of the cylindrical body 234. A wing 236 extends from the cylindrical body 234 and is situated in the central slot 220. A stabilizing bar 238 situated in slot 222 passes through an aperture in the wing 236 to stabilize the foot and eliminate any movement of the foot other than translation up and down. A brim 240 extends out and down from the portion of the cylindrical body 152 not in contact with the inner face 208. An inner cavity 242 enclosed by the brim 240 is configured to receive a portion of the anchor housing 20 therein. The front of brim 240 descends lower than the sides such that a rod recess 244 is formed between the coupling arm 202 and the brim front to help capture and guide the rod into the rod channel 22. An opening 246 in the front of the foot 232 provides a view into the foot to permit viewing of a preloaded locking cap 16 (not shown).

Figure 17:
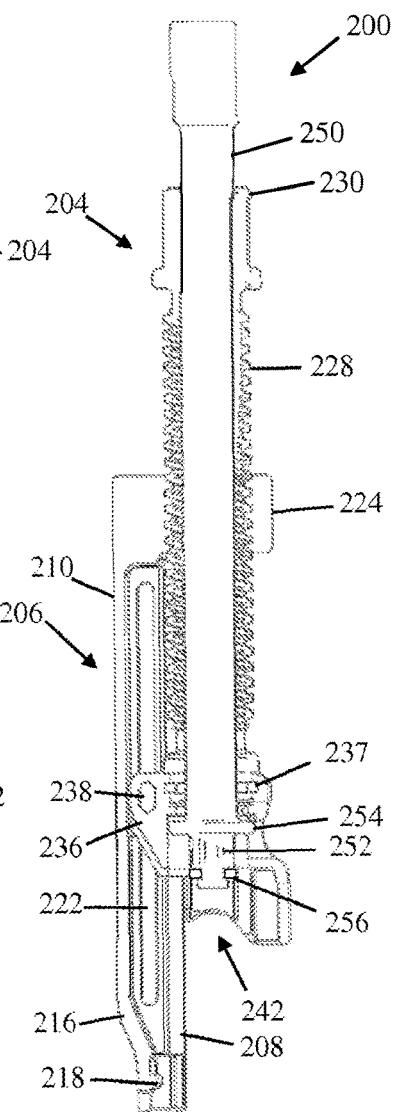
FIG. 17 is a cross-section view of the example rod reducer of FIG. 13 as viewed in FIG. 16.

With reference to FIG. 17, the translation unit 204 further includes a passage 248 extending from the drive nut 230 to the foot 232 in which a drive shaft 250 having a distal drive feature 252 is situated. A rim 254 above the drive feature maintains the drive feature within the foot 232. The drive shaft is permitted to freely translate a limited distance within the passage 248 such that the locking cap may be engaged and fully advanced into the anchor housing 20. An expansion ring 256 situated in a groove just below the drive feature 252 maintains the locking cap 16 on the drive feature 252 (FIG. 19) until the locking cap 16 is engaged in the housing, after which the drive feature 252 may be removed from the locking cap by pulling up on the drive shaft.

In use the reducer 200 is used similarly to the reducer 100 but without the-quick advance translation. Again, anchors 12 are implanted in each of the vertebra to be fixed and the rod is inserted to the anchor housings. The distal end of the coupling arm 202 is advanced onto an arm of the anchor housing 20 until the engagement features 216 on the coupling arm 202 engage with the engagement feature 26 of the housing 20. The coupling arm 202 is coupled to the housing with the foot 232 of the translation unit 204 spaced proximal to the housing 20 and the rod 14. A handle may be coupled to the drive nut 230 and the threaded shaft 228 rotated to advance the threading through the threaded passage 226 translating the foot 232 distally until the rod 14 is fully seated in the anchor housing 20. Again, though shown as a two level construct, additional anchors can be implanted to extend the construct 10 over multiple levels and/or bilaterally. After the rod 14 is fully seated in housing 20, the drive shaft 250 can be pressed downward and rotated to engage the locking cap 16 with the locking engagement feature 24 to capture and lock the rod 14 to the anchor 12.

With reference to FIGS. 20-30, a reducer 300 according to a third example embodiment is illustrated. The reducer 300 is configured to couple to an implanted anchor housing 20 and impart a downward force on the rod 14. The downward force on the rod acts to draw the rod and housing 20 together until the rod 14 fully seats in the rod channel 22. A locking mechanism, such as locking cap 16, may then be at least partially engaged to capture the rod 14 in the housing 20 prior to decoupling the reducer 100 from the anchor 12. As illustrated in FIGS. 20-21, the reducer 300 includes a coupling unit 302 unit that connects to the anchor 12 and a translation unit 304 that translates relative to the coupling unit 302 to urge the rod 14 towards the anchor. The coupling unit 302 includes an outer sleeve 306 and a translation coupler 308. The outer sleeve 306 has a generally centralized and cylindrical body 310. A connector mast 312 extends proximally from the body 310 and a pair of anchor coupling arms 316 extend distally from the body. The connector mast 312 is capped by a head 314 that is configured to engage with additional instruments if desired. By way of example, the head is configured to mimic the proximal end of the minimally invasive guides described in U.S. patent application Ser. Nos. 13/456,210, and 14/631,389 (the entire contents of which are incorporated by references as if set forth herein in their entireties) such that any instruments that engage or couple with the guides may also engage or couple with the reducer 300 (for example, vertebral body derotation assemblies, counter torques, etc.). The anchor coupling arms 316 are separated by a channel 318 that aligns with the anchor rod channel 22 when the reducer 300 is coupled to the anchor 12. To couple to the anchor 12, a cavity 320 at the distal end of the coupling arms 316 is dimensioned to snugly receive the arms of the anchor housing 20 therein. An engagement feature 322 is included on each coupling arm. By way of example, the engagement feature 322 includes a flexible finger 324 formed in the coupling arm and having a distal ridge 326 that projects into the cavity 320 to engage the engagement features 26 of the housing 20. The distal surface of the ridges 326 are tapered to automatically deflect the finger 324 outward as the arms of housing 20 are advanced into cavity 320, permitting the ridges 326 to pass the tops of the housing arms until they engages the anchor features 26. This way, the reducer 300 can be positioned over the rod and quickly snapped onto and secured to the anchor with the simple application of downward pressure. To later disengage the reducer 300 from the housing 20 an instrument may be advanced into the channel and manipulated to apply outward pressure to each of the fingers 324.

The body 310 is split into four quadrants including a front wall 328, a back wall 330, and two sidewalls 332. Four elongated side slots 334 separate each wall from the next. An elongated front slot 336 also runs through the middle of the front wall 328. The back wall 330 includes a ridge track 338, having a series of downward pointing ridges 340. That is, the ridges 340 have an upper surface that slopes aggressively away and down from the back wall 330. The lower surface of ridges 340 may be perpendicular to the outer face, or preferably, may slope mildly also away and down from the back wall 330.

The translation coupler 308, shown in FIG. 29, includes an internally threaded ring 342 surrounded by a front plate 344 and a back plate 346. Bars 348 couple the front plate 344 and back plate 346 together and engage cutouts in the outer surface of threaded ring 342 to longitudinally and rotationally fix the ring 342 in position relative to the front and back plates. The bars 348 can slide along the ring 342 cutouts such that the front plate 344 can be moved towards the ring 342 causing the back plate 344 to move farther away from the ring 342, and vice versa. The bars 348 couple the front and back plates through the side slots 334 such that the translation coupler 308 is coupled to body 310 and can translate up and down along the body 310 with the front plate 344 moving along the front wall 328 and the back plate 346 moving along the back wall 330. The inner surface of the back plate 346 includes a row of ridges 350 that are complementary to the ridges 340 of ridge track 338 and thus, inhibit upward or proximal translation of the translation coupler 308 when the ridges 350 and 340 are engaged. The inner surface of the front plate 344 includes a pair of cylindrical spring housings 352 situated centrally one on top of the other. The cylindrical spring housings 352 are dimensioned to pass through the front slot 336. The springs 354 fitted in the housings 352 engage the threaded ring 342 to bias the front plate 344 away from the front wall 328 and the back plate 346 into contact with the back wall 330 and hence the ridge track 338. In this configuration, the application of downward force causes ridges 350 to slide down the sloped upper surfaces of each ridge 340 and automatically return to the engaged position when the ridge 350 passes the lower surface of the ridge 340. Thus, the translation coupler 308 can be advanced distally by the application of downward force, but requires a user to manipulate front plate 344 to disengage the back plate 346 from the back wall 330 and allow proximal translation. Other configurations for lockingly engaging the back plate 346 to the back wall are also contemplated. For example only, instead of the ridge track 338, the side slots 334 adjacent the back wall can have circular cutouts along the slot length. A pair of cylindrical bars can be used on each side to connect the front and back plates instead of the single flat bar 348, the cylindrical bars passing through cylindrical cutouts in the threaded ring 342, and connecting to the back plate 346 via enlarged cylindrical discs that are dimensioned to slide laterally into the circular cutouts but cannot pass from one cutout to the next along the slot 334.

With reference to FIG. 28, the translation unit 304 includes a shaft 356 capped with a drive nut 358 at the proximal end and a pusher member 360 ending in a pair of reduction arms 362 at the distal end. The reduction arms 362 are situated between the coupling arms 316 and align with the channel 318 on each side. The distal ends of reduction arms 362 are preferably concave in shape to contour to the rod. Protrusions 364 just above each reduction arm 360 on the pusher member 360 slide along the channel 318 between the coupling arms 316 to prevent rotation of the pusher member 360. Along the shaft 356 between the drive nut 358 and pusher member 360 is a threaded region with threading complementary to the threaded ring 342 to translate the translation unit 304 relative to the coupling unit 302 upon rotation of the shaft 356. The drive nut 148 can be engaged by a handle (not shown) to facilitate rotation. The pusher member 360 is coupled to the threaded shaft 356 in such a way that the pusher member and shaft are fixed longitudinally but freely rotatable relative to each other. To accomplish this, by way of example, the distal end of the threaded portion includes flexible fingers 366 each having a ridge 370 that is received in an internal groove 368 of the pusher member 360. A passage 372 extends through the translation unit 104 from the drive nut 148 to reduction arms 360 to receive locking cap 16 and a driver therethrough to engage the locking cap 16 to the housing 20 prior to removing the reducer 300. Alternatively, the translation unit 304 may further be configured to carry a preloaded locking cap, for example, as described and illustrated with respect to reducer 200.

Figure 30A:
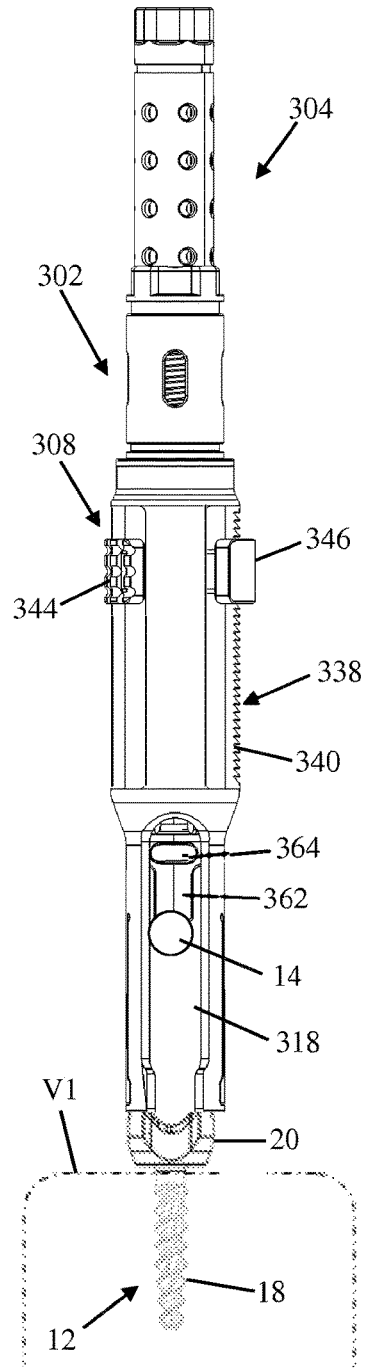
FIGS. 30A-30C are side views of the example reducer of FIG. 20 depicting a sequence for reducing a rod, according to one example embodiment.
Figure 30B:
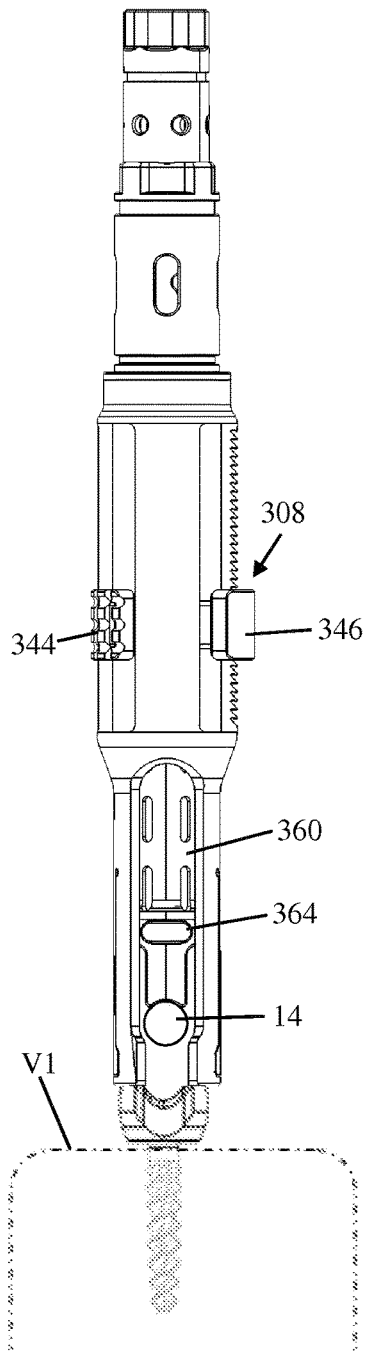
Figure 30C:
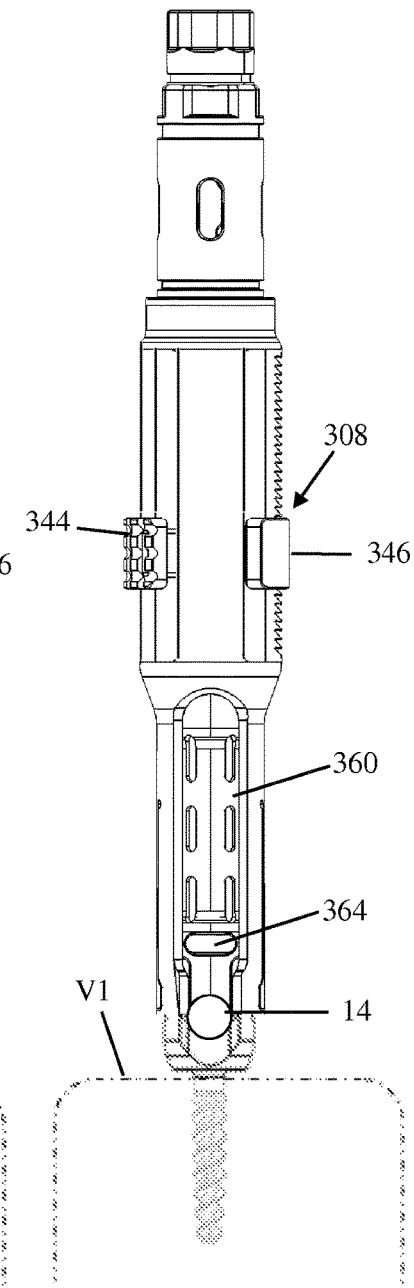
Figure 31:
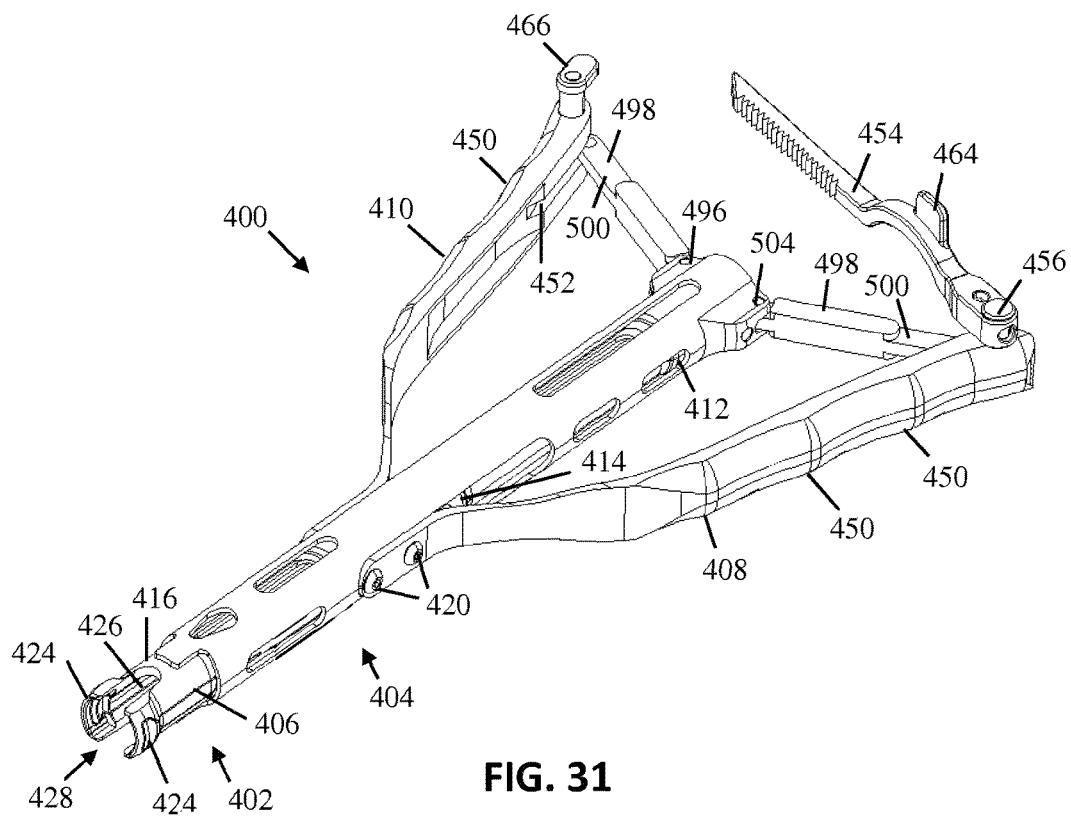
FIG. 31 is a perspective view of a rod reducer according to a fourth example embodiment.

Turning to FIGS. 30A-30C, use of the reducer 300 is illustrated by way of example. Anchors 12 are implanted in each of the vertebra to be fixed, including anchor 12 in vertebra V 1 which is the anchor to be reduced in this example, and the rod is inserted to the anchor housings. As seen in FIG. 30A, the distal ends of the coupling arms 316 are advanced over the rod such that the rod 14 is captured in the channel 318 and onto the anchor housing 20 until the engagement features 324 engage the features 26 on the housing. The user can then direct force distally onto the translation unit 304 such that the translation coupler 308 translates distally along the body 310 (translating the translating unit 304 distally along with it). Thus, the translation coupler 308 acts as quick-advance mechanism to advance the translation unit 304 without requiring the added effort and time required to threadingly advance the shaft 356 through the threaded ring 342. As the translation coupler 308 and translation unit 304 are advanced, the back plate ridges 350 engage each ridge 340 on the track 338 in turn to prevent unwanted proximal translation. The translation coupler 308 and translation unit 304 can be advanced this way until the translation unit bottoms out on the slots 334, the reduction arms 360 reach the rod 14 (FIG. 30B), or beyond that, the force required to further move the rod becomes too great or a more controlled and precise reduction is desired. With the reduction arms 360 in contact with the rod 14, the threaded shaft 356 is rotated to advance the threading through the threaded ring 342 until the rod is fully seated in the anchor housing 20, as shown in FIG. 30C. Though shown as a two level construct, additional anchors 12 can be implanted in additional vertebrae to extend the construct 10 over multiple levels and/or bilaterally with additional anchors 12 and another rod 14 implanted on the contralateral side of the vertebrae. The reducer 300 may be used on any or all of the anchors 12 in the construct. After the rod 14 is fully seated in housing 20 a locking cap 16 can be engaged with the locking engagement feature 24 to capture and lock the rod 14 to the anchor 12. The front plate 344 can then be depressed to disengage the back plate from the track 338 to retract the translating unit 104 if desired, and the reducer 300 disengaged from the housing 20.

With reference to FIGS. 31-36, a reducer 400 according to a fourth example embodiment is illustrated. The reducer 400 is configured to couple to both arms of anchor 12 and impart a downward force on the rod 14. The downward force on the rod acts to draw the rod and anchor housing 20 together until the rod 14 fully seats in the rod channel 22. A locking mechanism, such as locking cap 16 may then be at least partially engaged to capture the rod 14 in the housing 20 prior to decoupling the reducer 400 from the anchor 12. The reducer 400 includes a coupling unit 402 that connects to the anchor 12 and a translation unit 404 that translates relative to the coupling unit 402 to urge the rod 14 towards the anchor.

The coupling unit 402 includes base member 406 and first and second handle arms 408, 410 attached to the base member 406. The base member 406 is an elongated, generally tubular member having a proximal portion 412, central portion 414, and a distal portion 416. The middle portion 414 includes two pairs of fixation apertures 418 positioned on opposite lateral sides of the base member 406. The fixation apertures 418 are each sized and dimensioned to receive a fixation element 420, which act to affix the first and second handle arms 408, 410 to the base member 406. Each pair of fixation apertures 418 are positioned within a generally planar surface 422 formed within the otherwise generally cylindrical central portion 414. The distal portion 416 (shown in greater detail in FIG. 34) includes a pair of anchor coupling arms 424 extending distally from the body. The anchor coupling arms 424 are separated by a channel 426 that aligns with the anchor rod channel 22 when the reducer 400 is coupled to the anchor 12. To couple to the anchor 12, a cavity 428 at the distal end of the coupling arms 424 is dimensioned to snugly receive the arms of the anchor housing 20 therein. An engagement feature 430 is included on each coupling arm. By way of example, the engagement feature 430 includes a flexible finger 432 formed in the coupling arm and having a distal ridge 434 that projects into the cavity 428 to engage the engagement features 26 of the housing 20. The flexible fingers 432 are biased outward when the translation unit is in the proximal most position, thus allowing the housing 20 to pass into the cavity 428 past the distal ridges 434. As the translation unit 404 begins to travel along the coupling unit 402, the fingers 432 are compressed by translating unit 404 such that the distal ridges 434 extend into the cavity 428 and engage the engagement features 26 of the housing 20. This way, the reducer 400 can be located over the rod 14 and quickly positioned onto the housing. Thereafter a slight squeeze to compress the handles will secure the reducer to the anchor housing.

The first and second handle arms 408, 410 each include a distal attachment portion 438, a middle flare portion 440, and a proximal grip portion 442. The distal attachment portion 438 is generally planar and includes a pair of fixation apertures 444 which are sized and dimensioned to receive a fixation element 420, which act to affix the first and second handle arms 408, 410 to the base member 406. The distal attachment portion 438 flushly mates with the generally planar surface 422 of the central portion 414 of the base member 406 such that fixation apertures 444 on the first and second handle arms 408 are in alignment with the fixation apertures 418 of the base member 406. Fixation elements 420 may then extend through both apertures to secure the first and second handle arms 408, 410 to the base member 406. In alternative configurations, for example, the handle arms 408, 410 may be coupled to the base member 406 by other suitable methods (e.g. welding). The middle flare portion 440 extends proximally outward from the attachment portion 438 so that a space is created between the proximal grip portion 442 and the body member 406. The middle flare portion 440 is configured to flex, allowing the proximal grip portion 442 to move inward in response to a compressive force applied thereto. The proximal grip portion 442 includes an outward facing surface 446 (i.e. facing away from the body member 406) and an inward facing surface 448 (i.e. facing toward the body member 406). The outward facing surface includes a series of ridges 450 that form a finger grip. The inward facing surface includes a recessed channel 452 sized and dimensioned to receive the first end 500 of the translation link 498 (FIG. 36).

It is to be understood that the various features of the first and second handle arms 408, 410 discussed to this point are present on both handle arms even if not explicitly shown in the accompanying figures. Features that are unique to one handle arm or the other will now be discussed in further detail. The first handle arm 408, by way of example, includes a moveable ratchet arm 454 that may be employed to maintain the compressive force applied by a user until the ratchet arm is released. The ratchet arm 454 is an elongated member that is pivotally attached to the proximal end of the first handle arm 408. This pivot attachment is achieved via a pivot pin 456 that extends through an aperture 458 formed in the proximal end of the ratchet arm 454 and is ultimately received within an attachment aperture 460 located at the proximal end of the first handle arm 408. The distal end of the ratchet arm 454 includes a series of ridges 462 formed on downward facing side. Each of the ridges 462 is proximally tapered and acts in concert with the ratchet post 466 on the second handle arm 410 to enable unidirectional advancement of the ratchet arm 454 while the ratchet arm 454 is engaged with the ratchet post 466 and a user is applying compressive force to the first and second handle arms 408, 410. A disengagement tab 464 is provided on the ratchet arm to allow the user to dissociate the ratchet arm 454 from the ratchet post 466. By way of example, the disengagement tab 464 is provided as a generally planar flange extending away from the ratchet arm 454.

The second handle arm 410 includes a ratchet post 466 coupled to the proximal end of the second handle arm 410 via a pin 468 that extends through central aperture 470 of the ratchet post 466 and ultimately received within attachment aperture 472 located at the proximal end of the second handle arm 410. Referring to FIG. 35, the ratchet post 466 includes a generally cylindrical stem 474 and a cap 476. The cap 476 provides a physical barrier to maintain torsional stability of the ratchet locking mechanism, preventing the ratchet arm 454 from becoming dislodged during use. The stem further includes a flange 478 extending away from the stem and configured to engage the ridges 462 on the ratchet arm 454. The flange 478 has a generally planar tapered surface 480 that acts in concert with the taper of the ridges 462 to allow unidirectional advancement of the ratchet arm during use.

The translation unit 404 includes a generally tubular body member 482 that is sized and configured to receive the base member 406 of the coupling unit 402 longitudinally therein. The translation unit 404 is then caused to translate distally along the outside surface of the coupling unit 402 so as to contact the rod 14 and reduce it into the housing 20. With reference to FIG. 36, body member 482 includes a distal portion 484, middle portion 486, and proximal portion 488.

Figure 32:
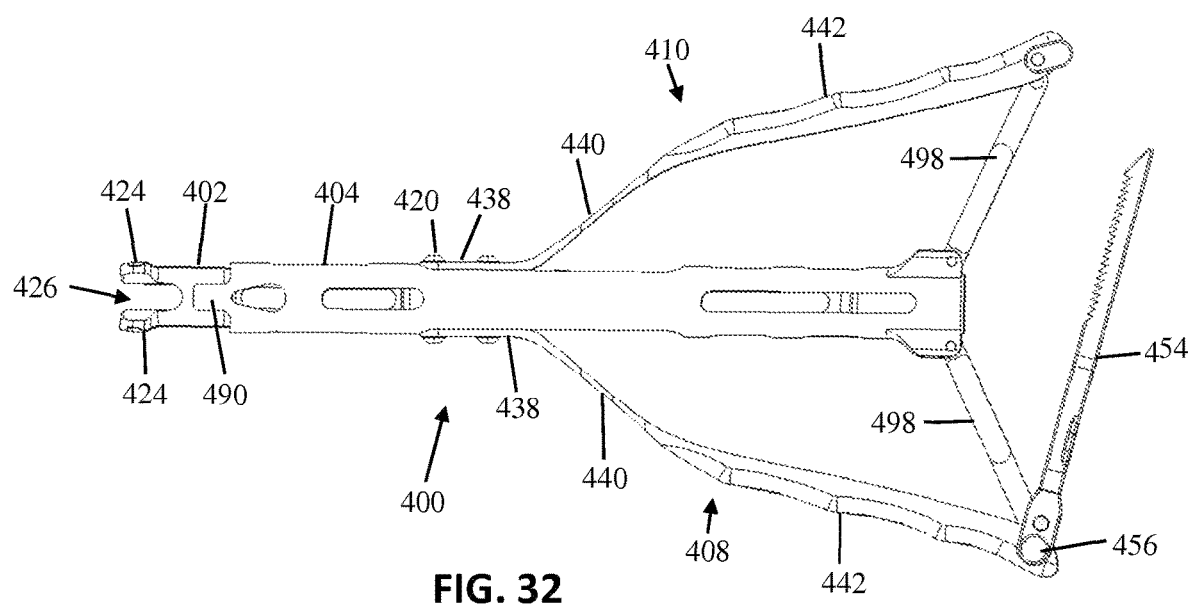
FIG. 32 is a top plan view of the example rod reducer of FIG. 31.
Figure 33:
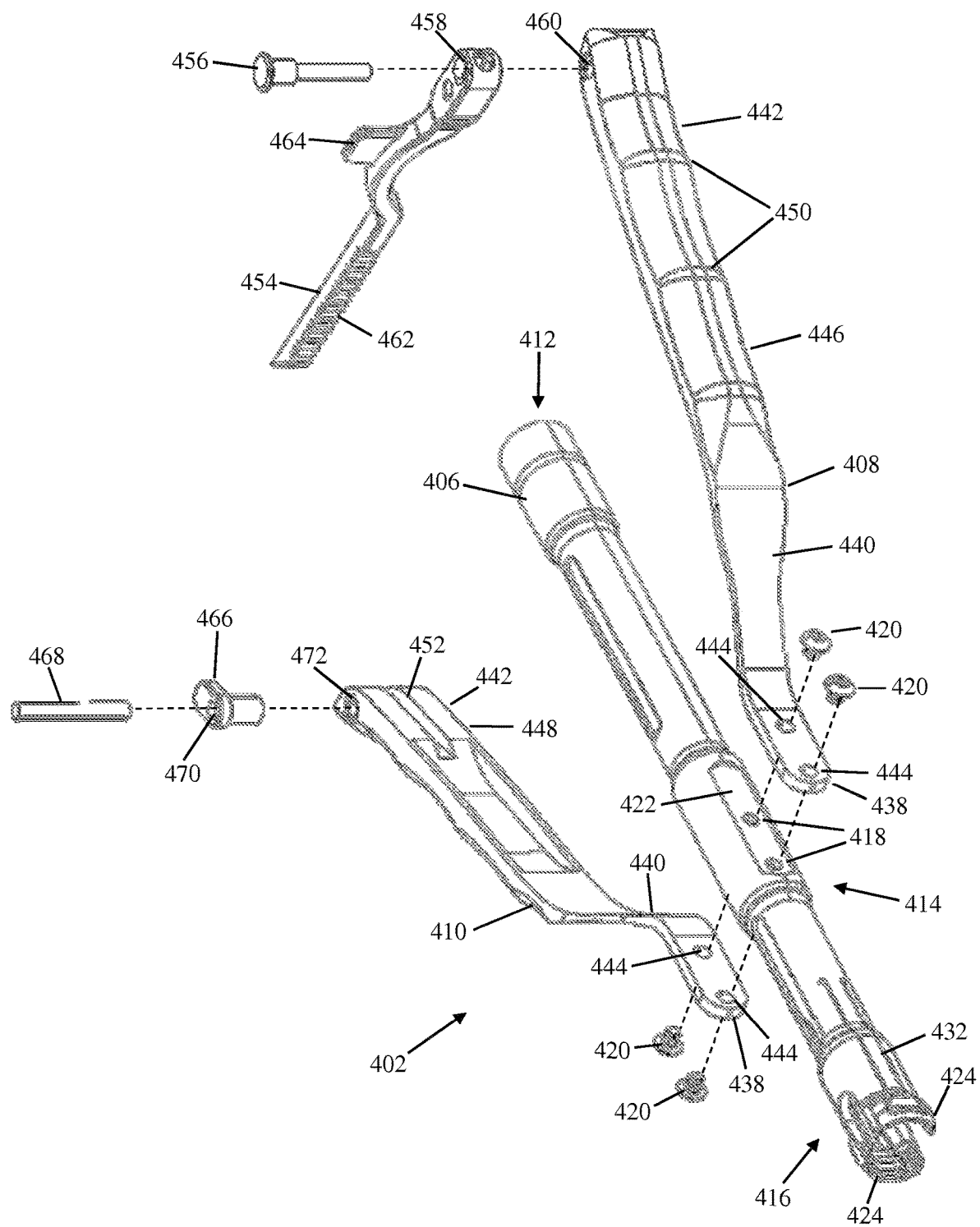
FIG. 33 is an exploded perspective view of a coupling unit forming part of the example rod reducer of FIG. 31.
Figure 37:
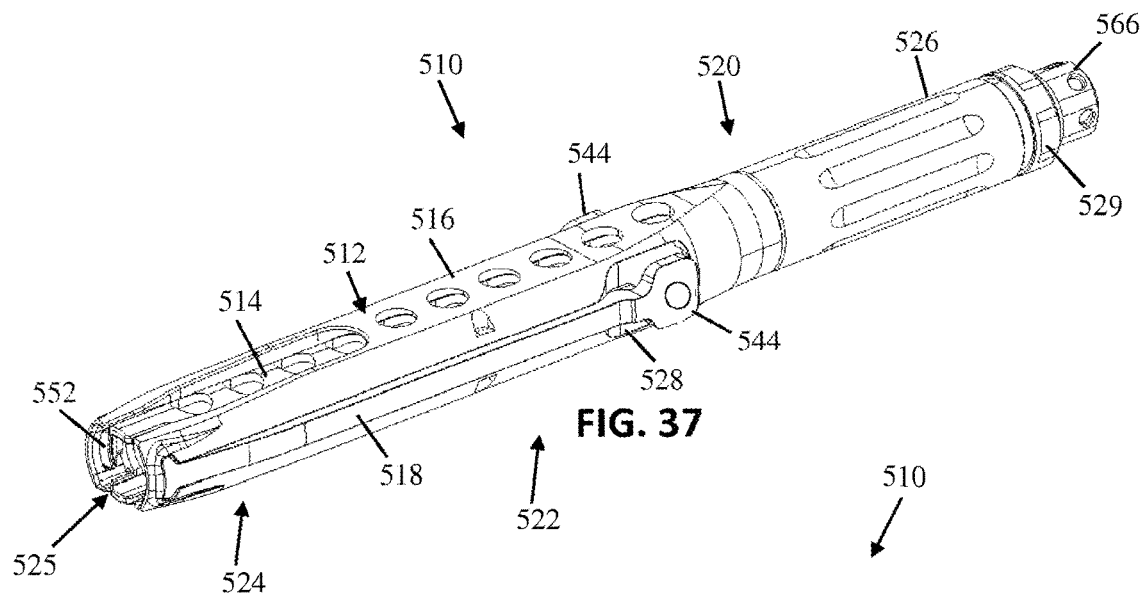
FIG. 37 is a perspective view of a rod reducer according to a fifth example embodiment.
Figure 38:
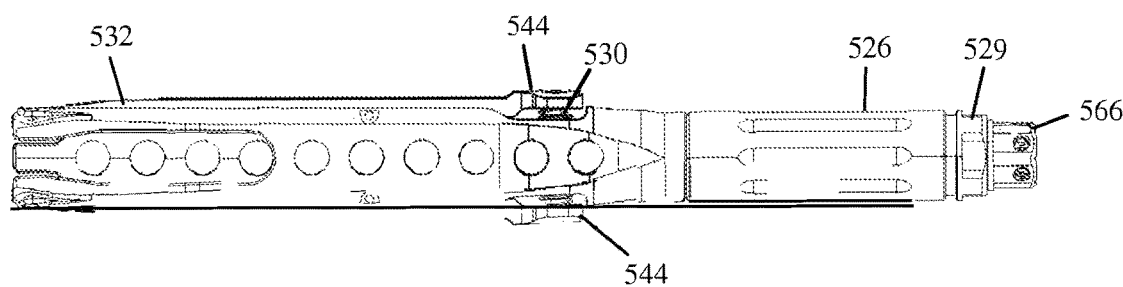
FIG. 38 is a plan view of the example rod reducer of FIG. 38.
Figure 39:
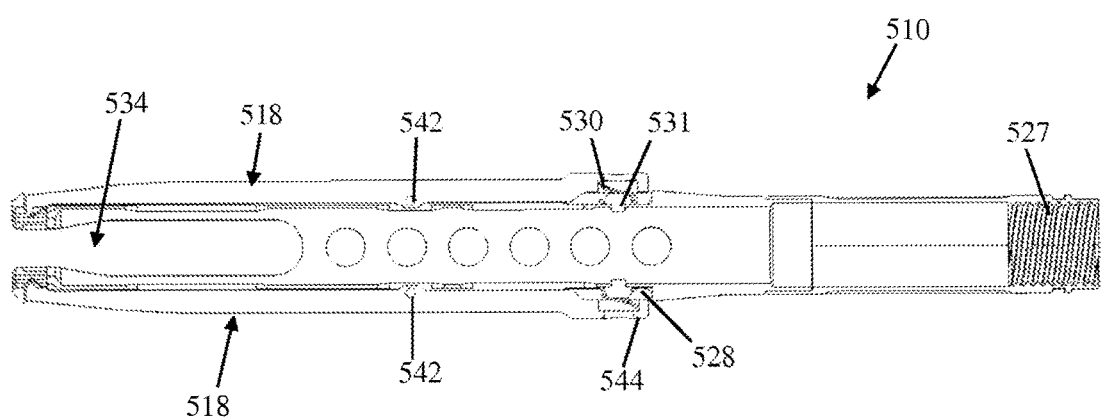
FIG. 39 is a sectional plan view of a coupling unit forming part of the example rod reducer of FIG. 37.
Figure 40:
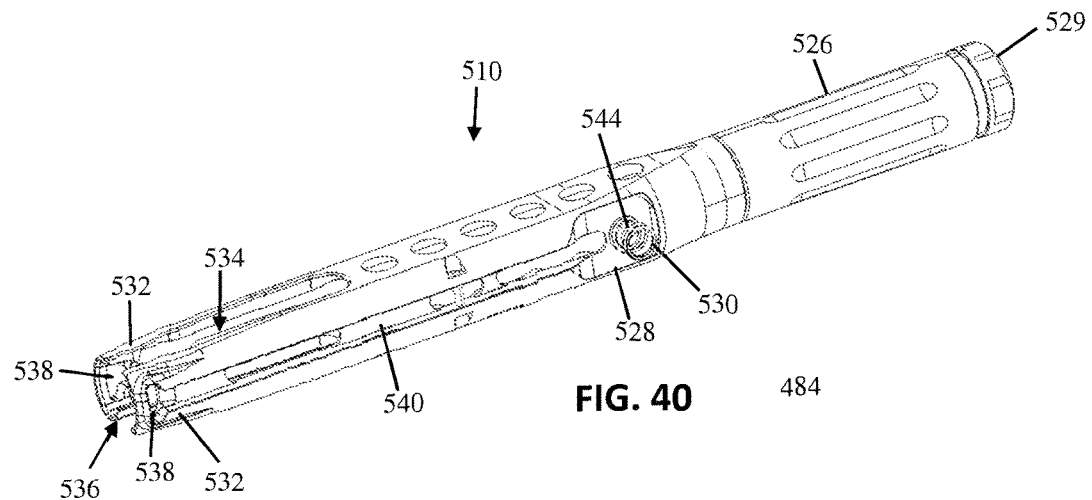
FIG. 40 is a perspective view of the coupling unit of FIG. 39 with an attachment feature removed.

The distal portion includes a pair of reduction arms 490 that are rotationally offset by ninety degrees from the coupling arms 424 such that the reduction arms 490 are aligned with the rod channel 426 (FIG. 32). The distal ends 492 of reduction arms 490 will contact the rod and may be configured with a shape (e.g. concave) to complement the contour of the rod 14. The middle portion 486 includes a pair of opposing elongated windows 494 extending along a substantial length of the middle portion 486. The elongated windows 494 are configured to receive the distal attachment portions 438 of the first and second handle arms 408, 410 therein and thus have a width dimension that is slightly larger than the width of the distal attachment portions 438. The elongated windows 494 permit the body member 482 to translate relative to the distal attachment portions 438. The interaction between the distal attachment portions 438 and the elongated windows 494 also provides torsional stability by helping to inhibit rotation of the translation unit 404 relative to the coupling unit 402.

The proximal portion 488 of the body member 482 includes a pair of attachment housings 496 positioned on either side of the body member 482 and serve as distal coupling points for the translation links 498. The translation links 498 extend between the proximal end of the translation unit 404 and the proximal ends of the handle arms 408, 410, and are pivotally attached at each end. The translation links 498 each include a first end 500 and a second end 502. The second ends 502 are received within the attachment housings 496 (one on each side of the body member 482) and are pivotally attached by way of a pin 504. The first ends 500 connect to the proximal ends of the first and second handle arms 408, 410 and are pivotally attached thereto by way of pins 456, 468, respectively. Compression applied to the grip 442 causes the grip to flex inward toward the base member 406 rotating the translation links 498, which causes the tubular body 486 to travel distally relative to the base member 406.

In practice, use of the reducer 400 is similar to the previously disclosed embodiments. Anchors 12 are implanted in each of the vertebra to be fixed, and the rod 14 is inserted into the anchor housings. The distal ends of the coupling arms 424 are advanced over the rod such that the rod 14 is captured in the channel 426 and onto the anchor housing 20. The user then directs a compressive force onto the first and second handle arms 408, 410 causing the proximal grip portions 442 of the handle arms to migrate inward, resulting in the distal translation of the body 486 along the coupling unit 402 with a downward force, resulting first in secure engagement between the housing 20 and the reducer 400, and thereafter reduction of the rod 14. As the translation unit 404 is advanced, the ridges 462 on the ratchet arm 454 engage the flange 478 on the ratchet post 466 to prevent unwanted proximal translation. Alternatively, the ratchet can be engaged after compression is applied by rotating the ratchet arm 454 out of engagement with the ratchet post 466 during compression and thereafter rotating the ratchet arm 454 into engagement with the ratchet post 466 to hold the compression. The translation unit 404 can be advanced this way until the rod 14 is fully seated in the housing 20. After the rod 14 is fully seated in housing 20 a locking cap 16 can be engaged with the locking engagement feature 24 to capture and lock the rod 14 to the anchor 12. To disengage the reducer 400 from the housing 20 compression on the handle arms 408, 410 is released causing the translation unit 404 to travel proximally and allowing the flexible arms to return to their natural position and disengage the housing 20.

Now with reference to FIGS. 37-43, a reducer 510 according to a fifth example embodiment is illustrated. The reducer 510 is configured to couple to both arms of anchor 12 and impart a downward force on the rod 14. The downward force on the rod acts to draw the rod and anchor housing 20 together until the rod 14 fully seats in the rod channel 22. A locking mechanism, such as locking cap 16 may then be at least partially engaged to capture the rod 14 in the housing 20 prior to decoupling the reducer 510 from the anchor 12. The reducer 510 includes a coupling unit 512 that connects to the anchor 12 and a translation unit 514 that translates relative to the coupling unit 512 to urge the rod 14 towards the anchor.

The coupling unit 512 includes a base member 516 and first and second attachment features 518 that are pivotally coupled with the base member 516. The base member 516 is an elongated, generally tubular member having a proximal portion 520, central portion 522, and a distal portion 524, and a central lumen 525 extending longitudinally through the entire length of the base member 516. The proximal portion 520 includes a handle 526 that provides a gripping area for a user to grip the reducer 510. Above the grip is a head 529 that allows the coupling of other instruments with the reducer 500. As with reducer 300 for example, the head 529 may be configured to mimic the proximal end of minimally invasive screw guides such that any instruments that engage or couple with the guides may also engage or couple with the reducer 500 (for example, vertebral body derotation assemblies, counter torques, etc.). The proximal portion 520 further includes a threaded portion 527 formed on the interior of the proximal portion 520 (i.e. the proximal end of the lumen 525) for threadedly engaging the translating unit 514. The central portion 522 includes a pair of lateral recesses 528 positioned opposite one another on either side of the base member 516. Each lateral recess 528 includes a spring 530 positioned therein and is adapted to receive a proximal end 544 of one attachment member 518. The spring 530 engages the proximal end 544 and functions to bias the attachment member 518 in a closed position, as will be explained. Guide pins 531 are located within the lateral recesses 528 and extend into the lumen 525. The guide pins 531 engage the guide slots 568 of the translation unit 514 to ensure that the pusher member of the translation unit 514 does not rotate during reduction. The distal portion 524 includes a pair of anchor coupling arms 532 extending distally from the body. The anchor coupling arms 532 are separated by a channel 534 that aligns with the anchor rod channel 22 when the reducer 510 is coupled to the anchor 12. To couple to the anchor 12, a cavity 536 at the distal end of the coupling arms 532 is dimensioned to snugly receive the arms of the anchor housing 20 therein. The distal portion 524 further includes a pair of lateral openings 538 positioned opposite one another near the distal end of the base member 516. The lateral openings 538 are adapted to allow passage of the distal ridge 552 of the attachment feature 518 to enable the distal ridge 552 to engage the housing 20. A pair of longitudinal recesses 540 is positioned on opposite sides of the base member 516 and extend from the central portion 522 to the distal portion 524, and more specifically from the lateral recesses 528 to the lateral openings 538. Each longitudinal recess 540 is dimensioned to receive the length of the attachment feature 518 therein which helps reduce the lateral profile of the reducer 510. A pivot pin 542 is positioned within each longitudinal recess 540 between the central portion 522 and the distal portion 524. The pivot pin 542 serves as a fulcrum about which the attachment feature 518 pivots.

Figure 41:
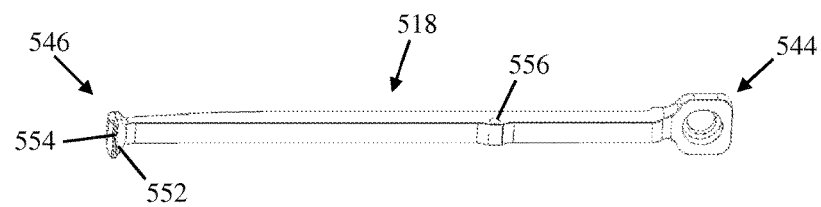
FIG. 41 is a perspective view of an attachment feature forming part of the coupling unit of FIG. 39.
Figure 42:
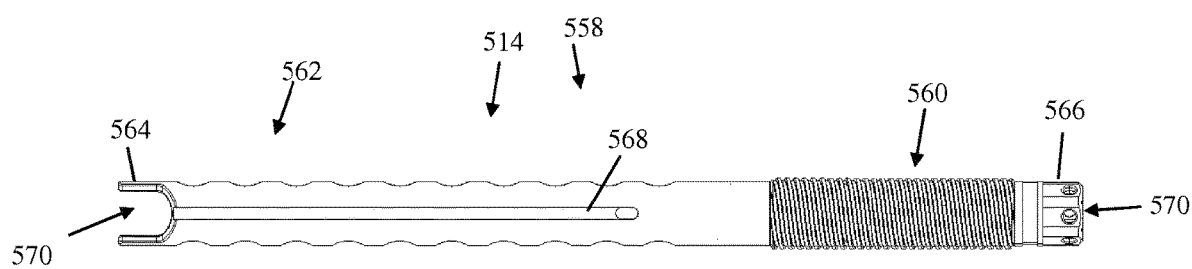
FIG. 42 is a plan view of a translating unit forming part of the example rod reducer of FIG. 37.
Figure 43:
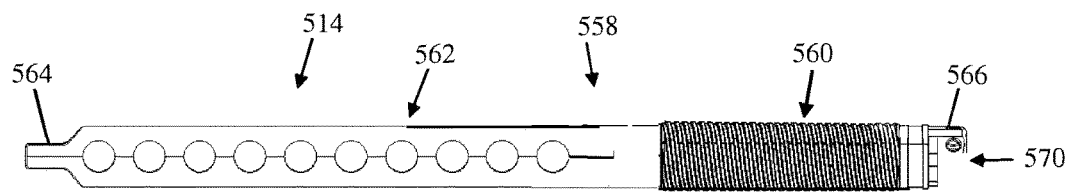
FIG. 43 is another plan view of the translating unit of FIG. 42.
Figure 44:
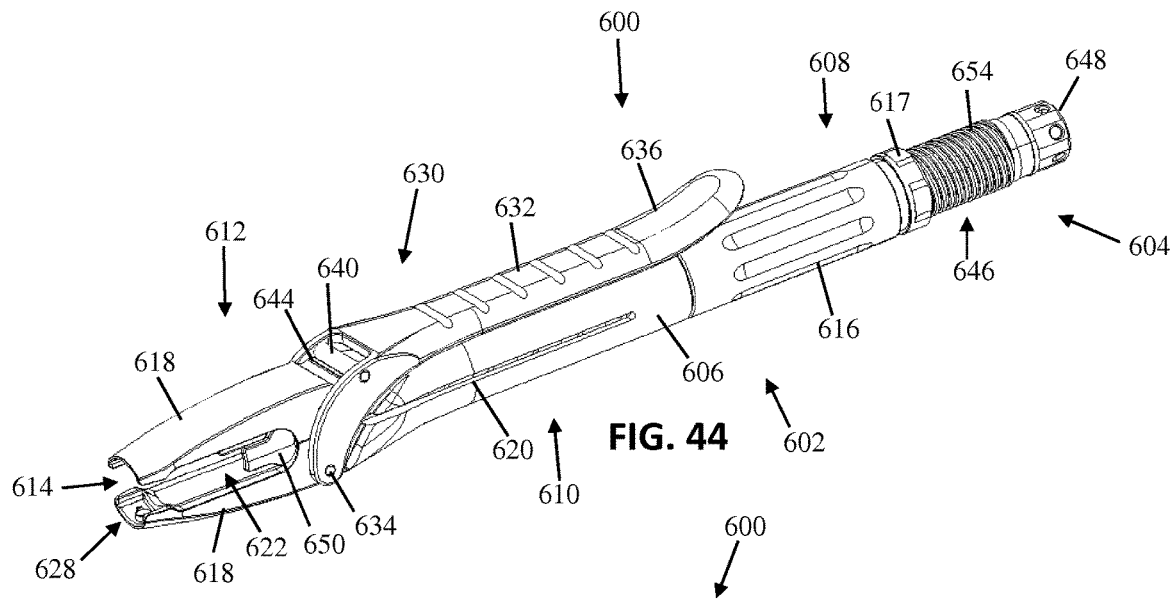
FIG. 44 is a perspective view of a rod reducer according to a sixth example embodiment.
Figure 45:
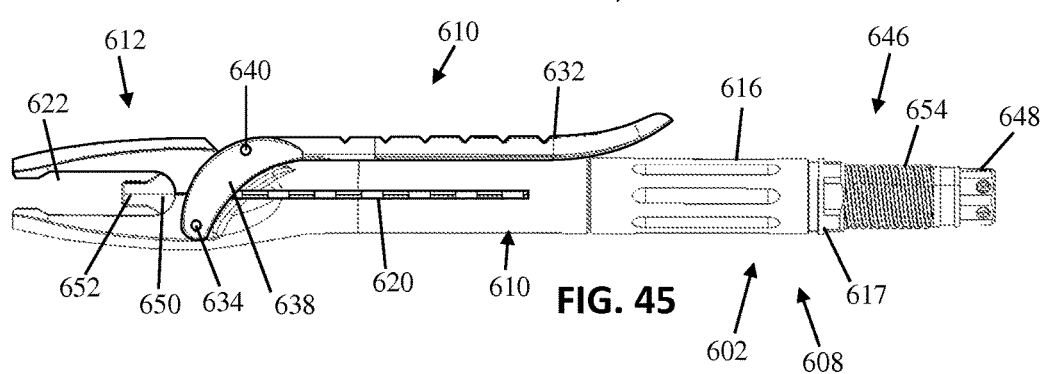
FIG. 45 is a side view of the rod reducer of FIG. 44.
Figure 46:
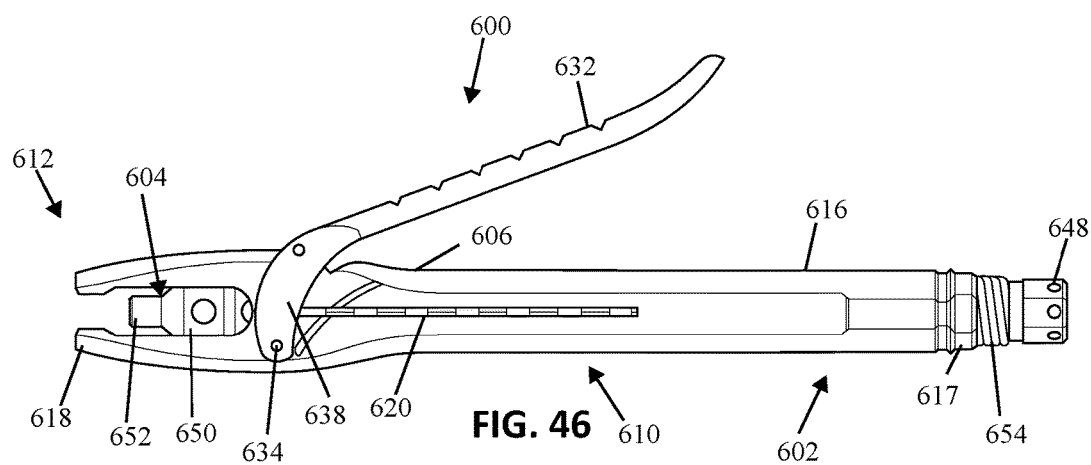
FIG. 46 is a side view of the rod reducer of FIG. 44 shown in an open or unlocked position.

The first and second attachment features 518 extend from the central portion 522 to the distal portion 524 along the lateral exterior of the base member 516, and are positioned within longitudinal recesses 540. FIG. 41 illustrates an attachment feature 518 in greater detail. Although described with reference to a single attachment feature 518, it is to be understood that each attachment feature 518 is identical. By way of example, each attachment feature 518 is a rigid, elongated member having a proximal end 544, a distal end 546, and a pivot 548. The proximal end 544 includes a recess 550 configured to receive at least a portion of spring 530 therein. The distal end 546 includes a distal ridge 552 that extends through the lateral opening 538 in the base member 516 and into the cavity 536 to engage the engagement features 26 of the housing 20. Each distal ridge 552 has a distal-facing tapered surface 554 that is inwardly tapered so as to automatically pivot the distal end 546 of the attachment feature 518 outward as the arms of the housing 20 are advanced into the cavity 536, permitting the ridges 552 to pass the tops of the housing arms until they engage the anchor features 26. Once the tops of the housing advance past the distal ridges 552, the ridges 552 encounter the anchor features 26. The spring 530 acts on the proximal end 544 to bias the distal ridges inward thus securing the engagement of ridges 552 into the anchor features 26, and hence, the reducer 510 to the housing 20. This way, the reducer 510 can be positioned over the rod 14 and quickly snapped onto and secured to the anchor with the simple application of downward pressure. The pivot 548 is positioned between the proximal end 544 and the distal end 546, preferably closer to the proximal end 544. By way of example only, the pivot 548 of the present example is positioned at a point located approximately one-third of the distance from the proximal end 544 to the distal end 546. The pivot 548 includes an aperture 556 dimensioned to receive the pivot pin 542 therethrough. To later disengage the reducer 510 from the housing 20, the user simply needs to apply a compressive force (e.g. using a thumb and forefinger) on the proximal ends 544 of the attachment features 518. This will cause the distal ends 546 to pivot outward and disengage the ridges 552 from the housing 20. The reducer 510 may then be removed.

The translation unit 514 includes a shaft 558 capped with a drive nut 566 at the proximal end and a pusher member 562 ending in a pair of reduction arms 564 at the distal end. The reduction arms 564 are situated between the coupling arms 532 and align with the channel 534 on each side. The distal ends of reduction arms 564 will contact the rod and may be configured with a shape (e.g. concave) to complement the contour of the rod 14. Along the shaft 558 between the drive nut 566 and pusher member 562 is a threaded region 560 with threading complementary to the inner threading 527 of the base member 516 to translate the translation unit 514 relative to the coupling unit 512 upon rotation of the shaft 558. The drive nut 566 can be engaged by a handle (not shown) to facilitate rotation. The pusher member 562 is coupled to the threaded shaft 558 in such a way that the pusher member and shaft are fixed longitudinally but freely rotatable relative to each other. Though not shown, this may be accomplished in the same manner described above with reference to translation unit 304 of reducer 300. That is the distal end of the threaded region may include multiple flexible fingers, each having a ridge that is received in an internal groove of the pusher member 562. The pusher member further includes a pair of guide slots 568 is positioned opposite one another on either side of the shaft 558 and extend proximally along the pusher member 562. The guide slots 568 are dimensioned to receive the guide pins 542 therein to prevent rotation of the pusher member 562 when the threaded portion 560 is rotated. A passage 570 extends through the translation unit 514 from the drive nut 566 to reduction arms 564 to receive locking cap 16 and a driver therethrough to engage the locking cap 16 to the housing 20 prior to removing the reducer 300. Alternatively, the translation unit 514 may further be configured to carry a preloaded locking cap, for example, as described and illustrated with respect to reducer 200.

In practice, use of the reducer 510 is similar to the previously disclosed embodiments. Anchors 12 are implanted in each of the vertebra to be fixed, and the rod 14 is inserted into the anchor housings. The distal ends of the coupling arms 532 are advanced over the rod such that the rod 14 is captured in the channel 536 and onto the anchor housing 20 until the engagement features 518 engage the features 26 on the housing. The user then attaches a handle or other suitable tool to the drive nut 566 of the translation unit 514. The user then rotates the handle (or other tool), causing the threaded region 560 of shaft 558 to advance distally through the threaded portion 527 of the coupling unit 512. This in turn causes the translation unit 514 as a whole to advance along the coupling unit 512 with a downward force, thereby advancing the rod 14 until the rod is fully seated in the housing 20. After the rod 14 is fully seated in housing 20 a locking cap 16 can be engaged with the locking engagement feature 24 to capture and lock the rod 14 to the anchor 12. To disengage the reducer 510 from the housing 20, the user simply needs to apply a compressive force (e.g. using a thumb and forefinger) on the proximal ends 544 of the attachment features 518. This will cause the distal ends 546 to pivot outward and disengage the ridges 552 from the housing 20. The reducer 510 may then be removed.

With reference to FIGS. 44-47, a reducer 600 according to a sixth example embodiment is illustrated. The reducer 600 is configured to couple to both arms of anchor 12 and impart a downward force on the rod 14. The downward force on the rod acts to draw the rod and anchor housing 20 together until the rod 14 fully seats in the rod channel 22. A locking mechanism, such as locking cap 16 may then be at least partially engaged to capture the rod 14 in the housing 20 prior to decoupling the reducer 600 from the anchor 12. The reducer 600 includes a coupling unit 602 that connects to the anchor 12 and a translation unit 604 that translates relative to the coupling unit 602 to urge the rod 14 towards the anchor.

The coupling unit 602 includes an elongated, generally tubular base member 606 including a proximal portion 608, a central portion 610, a distal portion 612, and a central lumen 614 extending longitudinally through the entire length of the base member 606. The proximal portion 608 includes a grip 616 that provides a gripping area for a user to grip the reducer 600 while reducing the spinal rod. Above the grip is a head 617 that allows the coupling of other instruments with the reducer 600. As with reducer 300 for example, the head 617 may be configured to mimic the proximal end of minimally invasive screw guides such that any instruments that engage or couple with the guides may also engage or couple with the reducer 600 (for example, vertebral body derotation assemblies, counter torques, etc.). The proximal portion 608 further includes a threaded portion (not shown but similar to threaded portion 527 of reducer 510) formed on the interior of the proximal portion 608 (i.e. the proximal end of the lumen 614) for threadedly engaging the translating unit 604. The distal portion 612 includes a pair of anchor coupling arms 618 extending distally from the body. A pair of slits 620 extend longitudinally along the base member 606 from the distal portion 612 to the central portion 610. The slits 620 define and separate the proximal portion of the anchor coupling arms 618, and allow the coupling arms 618 to clamp together during use. The anchor coupling arms 618 are separated by a channel 622 that aligns with the anchor rod channel 22 when the reducer 600 is coupled to the anchor 12. To couple to the anchor 12, a cavity 624 at the distal end of the coupling arms 618 is dimensioned to snugly receive the arms of the anchor housing 20 therein. The distal ends of the coupling arms 618 each include a distal ridge 626 and a post 628 for engaging complementary features on the housing 20. The coupling arms 616 are configured to move from a first open position (FIG. 46) in which the arms 618 are naturally biased apart to allow the housing to pass completely into the cavity 624. Thereafter the coupling arms are maneuvered into a closed position (FIG. 44) in which the engagement features on the coupling arms engage the features on the housing, securing the reducer 600 to the housing.

To maneuver the coupling arms from the open position to the closed position, the reducer utilizes a cam-over mechanism that forces the coupling arms 618 closed. By way of example only, the cam-over mechanism 630 comprises a lever arm 632 that is pivotally attached to one of the coupling arms 618 via a pair of pivot pins 634. The proximal region of the pivot arm 632 comprises a handle 636 configured for manipulation by a user. The distal region of the pivot arm 632 includes a pair of distally extending flanges 638 that each extend to an opposite lateral side of a first of the coupling arms 618 (also to be referred to as the inferior coupling arm 618). The pivot pins 634 are each located at the distal end of a respective flange 638 and pivotally couple the flanges 638 to both sides of the inferior coupling arm 618. A locking bar 640 extends across the void between the flanges 638 near the proximal ends of the flanges 638. The locking bar 640 travels along the cam surface formed in the top surface of the second of the coupling arms 618 (also to be referred to as the superior coupling arm 618) when the lever arm 632 is rotated from the open position to the closed position. The cam surface includes a first groove 642 and a second groove 643 separated by lip 644. When the locking bar 640 rests in the first groove 642, the coupling arms 618 are allowed to rest in their naturally biased open position. Then, as the bar 640 travels over the lip 644 the coupling arms are compressed (securing the housing between the coupling arms) with the locking bar 640 ending up in a stable resting position in the second groove 643 with the arms still compressed. Passage of the bar 640 over the lip 644 and into second groove 643 may also provide tactile feedback to the user that indicates the device is locked. To unlock the attachment feature 630, the user pulls the lever arm 632 away from the body member 606 with sufficient force to overcome the resistance of the lip 644.

The translation unit 604, includes a shaft 646 capped with a drive nut 648 at the proximal end and a pusher member 650 ending in a pair of reduction arms 652 at the distal end. The reduction arms 652 are situated between the coupling arms 618 and align with the channel 622 on each side. The distal ends of reduction arms 652 will contact the rod and may be configured with a shape (e.g. concave) to complement the contour of the rod 14. Along the shaft 646 between the drive nut 648 and pusher member 650 is a threaded region 654 with threading complementary to the inner threading of the base member 606 to translate the translation unit 604 relative to the coupling unit 602 upon rotation of the shaft 646. The drive nut 648 can be engaged by a handle (not shown) to facilitate rotation. The pusher member 650 is coupled to the threaded shaft 654 in such a way that the pusher member and shaft are fixed longitudinally but freely rotatable relative to each other. Though not shown, this may be accomplished in the same manner described above with reference to translation unit 304 of reducer 300. That is the distal end of the threaded region may include multiple flexible fingers, each having a ridge that is received in an internal groove of the pusher member 650. Pins through the base member 606 engage a pair of guide slots (not shown) positioned opposite one another on either side of the shaft 646 that extend proximally along the pusher member 650. The guide slots receive the guide pins therein to prevent rotation of the pusher member 650 when the threaded portion 654 is rotated. A passage 656 extends through the translation unit 604 from the drive nut 648 to reduction arms 652 to receive locking cap 16 and a driver therethrough to engage the locking cap 16 to the housing 20 prior to removing the reducer 600. Alternatively, the translation unit 614 may further be configured to carry a preloaded locking cap, for example, as described and illustrated with respect to reducer 200.

In practice, use of the reducer 600 is similar to the previously disclosed embodiments. Anchors 12 are implanted in each of the vertebra to be fixed, and the rod 14 is inserted into the anchor housings. With the lever arm 632 in the "open" position, the distal ends of the coupling arms 618 are advanced over the rod such that the rod 14 is captured in the channel 622 and onto the anchor housing 20 until the engagement features on the coupling arms 618 engage the corresponding features 26 on the housing. The user then maneuvers the lever arm 632 from the open position to the closed and locked position by applying enough force to urge the locking pin 640 over the lip 644 and into the recess 642. The user then rotates the handle (or other tool), causing the threaded region 654 of shaft 646 to advance distally through the threaded portion of the coupling unit 602. This in turn causes the translation unit 604 as a whole to advance along the coupling unit 602 with a downward force, thereby advancing the rod 14 until the rod is fully seated in the housing 20. After the rod 14 is fully seated in housing 20 a locking cap 16 can be engaged with the locking engagement feature 24 to capture and lock the rod 14 to the anchor 12. To disengage the reducer 600 from the housing 20, the user simply needs to pull the lever arm 632 away from the body member 606 with sufficient force to overcome the resistance of the lip 644. The reducer 600 may then be removed.

FIGS. 48-51 illustrate an example of an additional accessory that can aid in positioning of the spinal rod during a spinal surgery. When placing and reducing the rod into an anchor at one level, it would be useful for the rod to be encouraged to find the housing members of nearby bone anchors at the same time that reduction is being performed on a particular anchor. By way of example, this may be particularly advantageous when constructing longer rod constructs as it may result in a reduction of time and effort required to seat the rod in each screw. FIGS. 47-50 illustrate one example of an anchor clip 660 that may be employed in such a manner. The anchor clip 660 is configured to attach to a housing 20 of an anchor at a spinal level adjacent (or several levels away) a spinal level at which reduction is actively performed (e.g. FIG. 51). Multiple anchor clips 660 can be used in conjunction with one or more reducers and in any configuration. By way of example, one scenario would include a pair of anchor clips 660 book-ended by a pair of reducers. In this configuration the time and effort required to reduce the rod may be cut by approximately half as the two interior anchors will not require direct reduction.

By way of example only, the anchor clip 660 includes a pair of arm members 662 and at least one bias member 664. Each arm member 662 has a proximal handle portion 666, a distal anchor coupling portion 668, and a hinge member 670 positioned between the proximal and distal portions. The proximal handle portions 666 of each arm member 662 extend proximally from the hinge member 670 and are separated from each other by a proximal space 672. The bias member 664 is positioned between the proximal portions 666 of the arm members 662, just proximal of the hinge member 670. In the present example, there are two bias members 664 in use, one positioned near each hinge member 670. In the instant example, the bias member 664 is a horseshoe-shaped spring having a curved end 674 and a pair of tabs 676 at the open end. The bias member 664 is oriented with the curved end 674 positioned nearest the hinge member 670. The tabs 676 are received within apertures formed in the arm members 662, with one tab mating with one arm member 662 and the other tab on the same bias member 664 mating with the other arm member 662. The tabs 676 prevent the bias member 664 from moving out of position during use.

The distal anchor coupling portions 668 of each arm member 662 extend distally from the hinge member 670 and are separated from each other by a distal space 678. The distal ends 680 of the arm members 662 are separated by a channel 682 that aligns with the anchor rod channel 22 when the anchor clip 660 is coupled to the anchor 12. To enable coupling with the anchor 12, a cavity 684 at the distal end 680 is dimensioned to snugly receive the arms of the anchor housing 20 therein. The distal end 680 further includes an engagement feature comprising a ridge 686 projecting into the cavity 684 to engage the engagement features 26 of the housing 20. A secondary engagement feature comprising a cylindrical post 688 may also be positioned within the cavity to engage a cylindrical recess formed in the housing 20. Each ridge 686 and the cylindrical post 688 has a distal-facing tapered surface that is inwardly tapered so as to automatically deflect the anchor coupling portions 668 outward as the arms of the housing 20 are advanced into the cavity 682, permitting the ridges 686 to pass the tops of the housing arms until they engage the anchor features 26. This way, the reducer anchor clip 660 can be positioned over the rod 14 and quickly snapped onto and secured to the anchor with the simple application of downward pressure. Alternatively, the user can simply squeeze the proximal handle portions 666 to spread the coupling portions 668 until the housing freely passes into the cavity 684. Thereafter the proximal handles are released allowing the engagement features to engage. Center passage 673 connects the proximal space 672 and distal space 678 to permit introduction of a lock screw into the housing 20 through the anchor clip 660. To disengage the anchor clip 660 from the housing 20 a user simply needs to apply compressive pressure to the proximal handle portions 666 of the anchor clip 660 again causing the distal coupling portions 668 to separate and allowing the clip 660 to be removed.

Figure 51:
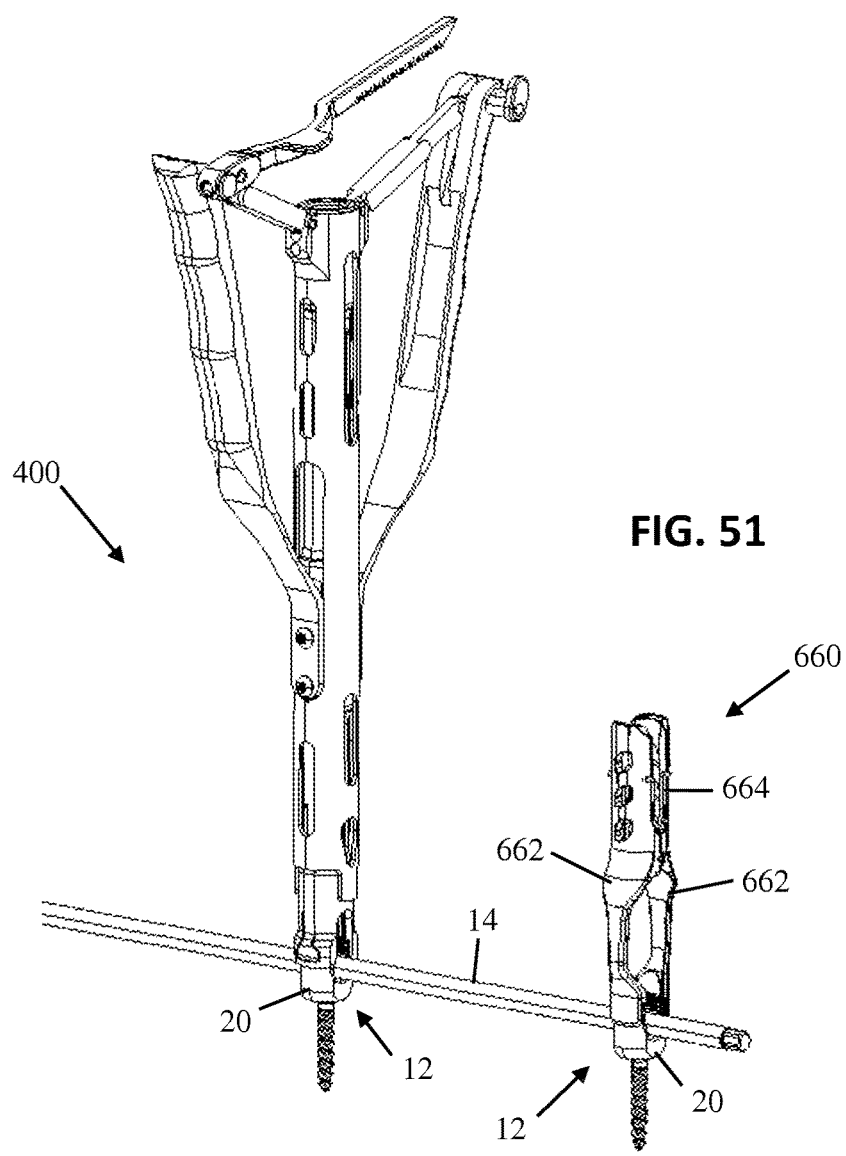
FIG. 51 is a perspective view of the anchor clip of FIG. 49 in use attached to a bone anchor adjacent to another bone anchor with a reducer attached.

The distal anchor coupling portions 668 flare outward and then inward between the hinge member 670 and the distal end 680. Because of this, the distal space 678 has a larger width than the channel 682 (or rod channel in the anchor housing 20). This feature advantageously allows more room for the clip to capture a spinal rod 14 that may not be aligned over the screw. Thereafter, when the anchor clip 660 is attached to a housing 20, the rod 14 remains "trapped" within the distal space 678 and the clip will direct the rod into alignment with the screw housing 20 as the rod is reduced (and/or bent) at the adjacent levels, as depicted in FIG. 51. FIG. 50 depicts an embodiment of the clip 660', wherein the spring biased proximal handle portions 666 are replace by a scissor clamp, but otherwise operates in the same manner.

Figure 52:
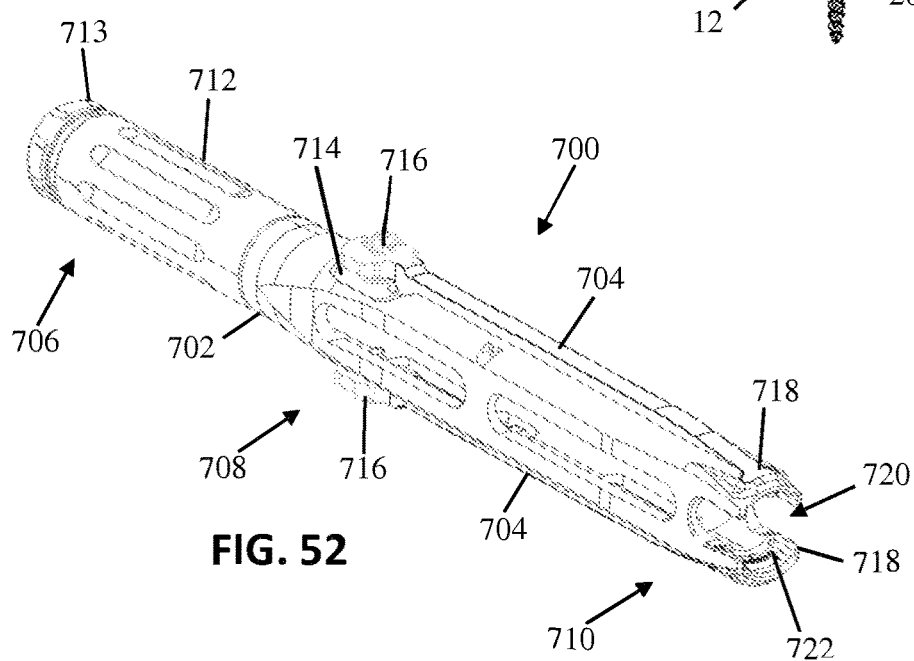
FIG. 52 is a perspective view of an anchor extension tower according to one example embodiment.

When constructing a spinal fixation construct there may circumstances where it is desirable to engage and manipulate the anchor housing prior to rod insertion or when no reduction is required. By way of one example, applying torque to an anchor implanted in a vertebra can be employed to move the vertebra, which, when the vertebra (or multiple vertebrae) are rotationally misaligned, can be effective in derotating the vertebra (or vertebrae) into a less detrimental position. With reference to FIG. 52, an example embodiment of an extension tower 700 for effectively increasing the height of the anchor housing 20 in order to manipulate the anchor form outside the patient is illustrated. The extension tower 700 is similar in construction to the coupling unit 512 of reducer 510 and includes a base member 702 and first and second attachment features 704 that are pivotally coupled with the base member 702. The base member 702 is an elongated, generally tubular member having a proximal portion 706, central portion 706, and a distal portion 710. The proximal portion 706 includes a handle 712 that provides a gripping area for a user to grip the extension tower 700 either by hand or with additional instrumentation. Above the grip is a head 713, like the heads previously described for reducers 300, 500, and 600, that allows the coupling of other instruments (e.g. derotation couplers or other tower linking devices, counter torques, etc.) to the tower 700. The central portion 708 includes a pair of lateral recesses 714 positioned opposite one another on either side of the base member 702. Each lateral recess 714 includes a spring 716 positioned therein and is adapted to receive a proximal end 730 of one attachment member 704. The spring 716 engages the proximal end 730 and functions to bias the attachment member 704 in a closed position, as will be explained. The distal portion 710 includes a pair of anchor coupling arms 718 extending distally from the body. The anchor coupling arms 718 are separated by a channel 720 that aligns with the anchor rod channel 22 when the extension tower is coupled to the anchor 12. To couple to the anchor 12, a cavity 722 at the distal end of the coupling arms 718 is dimensioned to snugly receive the arms of the anchor housing 20 therein. The distal portion 710 further includes a pair of lateral openings 724 positioned opposite one another near the distal end of the base member 702. The lateral openings 724 are adapted to allow passage of the distal ridge 738 of the attachment feature 704 to enable the distal ridge 738 to engage the housing 20. A pair of longitudinal recesses 726 are positioned on opposite sides of the base member 702 and extend from the central portion 708 to the distal portion 710, and more specifically from the lateral recesses 714 to the lateral openings 724. Each longitudinal recess 726 is dimensioned to receive the length of the attachment feature 704 therein to help reduce the lateral profile of the extension tower 700. A pivot pin 728 is positioned within each longitudinal recess 726 between the central portion 708 and the distal portion 710. The pivot pin 728 acts as a fulcrum about which the attachment feature 704 pivots.

The first and second attachment features 704 extend from the central portion 708 to the distal portion 710 along the lateral exterior of the base member 702, and are positioned within longitudinal recesses 726. Although described with reference to a single attachment feature 704, it is to be understood that each attachment feature 704 is identical. By way of example, each attachment feature 704 is a rigid, elongated member having a proximal end 730, a distal end 732, and a pivot 734. The proximal end 730 includes a recess 736 configured to receive at least a portion of spring 716 therein. The distal end 732 includes a distal ridge 738 that extends through the lateral opening 724 in the base member 702 and into the cavity 722 to engage the engagement features 26 of the housing 20. Each distal ridge 738 has a distal-facing tapered surface 740 that is inwardly tapered so as to automatically deflect the attachment feature 704 outward as the arms of the housing 20 are advanced into the cavity 722, permitting the ridges 738 to pass the tops of the housing arms until they engage the anchor features 26. Once the tops of the housing advance past the distal ridges 738, the ridges 738 encounter the anchor features 26. The spring 716 acts on the proximal end 730 to bias the distal ridges inward thus securing the engagement of ridges 738 into the anchor features 26, and hence, the extension tower 700 to the housing 20 of screw 12. This way, the extension tower 700 can be positioned quickly snapped onto and secured to the anchor with the simple application of downward pressure. The pivot 734 is positioned between the proximal end 730 and the distal end 732, preferably closer to the proximal end 730. By way of example only, the pivot 734 of the present example is positioned at a point located approximately one-third of the distance from the proximal end 730 to the distal end 732. The pivot 734 includes an aperture 742 dimensioned to receive the pivot pin 728 therethrough. To later disengage the extension tower 700 from the housing 20, the user simply needs to apply a compressive force (e.g. using a thumb and forefinger) on the proximal ends 730 of the attachment features 704. This will cause the distal ends 732 to pivot outward and disengage the ridges 738 from the housing 20. The tower 700 may then be removed from the area.

While specific embodiments have been shown by way of example in the drawings and described herein in detail, it will be appreciated that the invention is susceptible to various modifications and alternative forms (beyond combining features disclosed herein). The description herein of specific embodiments is not intended to limit the invention to the particular forms disclosed, but on the contrary, the invention is to cover all modifications, equivalents, and alternatives falling within the spirit and scope of the invention.

What is claimed is:

1. A rod reducer for reducing a spinal rod to a rod-capturing portion of a fixation anchor, the rod reducer comprising:
   a coupling unit configured to engage the fixation anchor, wherein the coupling unit comprises:
     a base member having a proximal portion, a central portion, a distal portion, and a lumen extending longitudinally through a length of the base member, wherein the distal portion includes a cavity configured to receive the fixation anchor therein, and
     a first attachment feature and a second attachment feature, each pivotally coupled to the base member, wherein the first and second attachment features each comprise an elongate member extending between the central portion and the distal portion of the base member; and
   a translation unit configured to engage the proximal portion of the base member and translate relative to the coupling unit, wherein the translation unit comprises:
     a shaft having an external thread and extending between a proximal end and a distal end,
     a drive nut coupled to the proximal end of the shaft,
     a foot having a pusher member coupled to the distal end of the shaft and configured to engage the spinal rod, and
     a ring with internal threading and engaging with the external threads of the shaft; and
     wherein the foot includes a cylindrical body that is coupled to the shaft and fixed longitudinally to the shaft but freely rotatable relative to each other.

2. The rod reducer of claim 1, wherein the distal portion of the base member comprises a pair of anchor coupling arms extending distally from the base member and separated by a channel to form the cavity.

3. The rod reducer of claim 1, wherein the base member of the coupling unit comprises:
   a first longitudinal recess and a second longitudinal recess that each extend between the central portion and the distal portion of the base member, wherein the first and the second longitudinal recesses are disposed circumferentially opposite one another, and are configured to receive the first and second attachment features therein, respectively; and
   a first lateral recess and a second lateral recess in the central portion, wherein the first and the second lateral recesses are circumferentially opposite one another, and are configured to receive a proximal end of the first attachment feature and a proximal end of the second attachment feature therein, respectively.

4. The rod reducer of claim 3, wherein the coupling unit further comprises a first spring and a second spring disposed within the first and second lateral recesses, respectively, wherein the first and second springs are configured to engage the proximal ends of the first and second attachment features, respectively, to bias the first and second attachment features into a closed position.

5. The rod reducer of claim 3, wherein the coupling unit further comprises a first guide pin and a second guide pin disposed within the first and second lateral recesses, respectively, and extending into the lumen, wherein the first and second guide pins are configured to engage the translation unit to limit rotation of the pusher member relative to the shaft.

6. The rod reducer of claim 3, wherein the coupling unit further comprises a first pivot pin and a second pivot pin disposed within the first and second longitudinal recesses, respectively, wherein the first and second attachment features are configured to pivot about the first and second pivot pins, respectively.

7. The rod reducer of claim 1, wherein each elongate member of the first and second attachment features comprises a distal end configured to engage the fixation anchor.

8. The rod reducer of claim 7, wherein the distal end of each elongate member comprises a distal ridge having a tapered surface configured to pivot the distal end of the respective attachment feature outward as the fixation anchor advances into the cavity.

9. The rod reducer of claim 1, wherein the external thread of the shaft is configured to threadably engage an internal thread on the proximal portion of the base member thereby causing the shaft to rotate and translate the translation unit relative to the coupling unit.

10. The rod reducer of claim 1, wherein a distal end of the pusher member comprises a pair of reduction arms configured to engage the spinal rod.

11. The rod reducer of claim 10, wherein the pusher member comprises a pair of guide slots extending proximally from the pair of reduction arms, wherein the pair of guide slots are configured to engage the coupling unit to limit rotation of the pusher member when the shaft rotates.

12. The rod reducer of claim 1, wherein the translation unit comprises a passage extending therethrough that is dimensioned to receive a locking cap configured to engage the fixation anchor to lock the spinal rod within the rod-capturing portion of the fixation anchor.

13. A system, comprising:
   a spinal rod;
   a fixation anchor having a rod-capturing portion; and
   a rod reducer for reducing the spinal rod to the rod-capturing portion of the fixation anchor, wherein the rod reducer comprises:
     a coupling unit configured to engage the fixation anchor, wherein the coupling unit comprises:
       a base member having a proximal portion, a central portion, a distal portion, and a lumen extending longitudinally through a length of the base member, wherein the distal portion includes a cavity configured to receive the fixation anchor therein, and a first attachment feature and a second attachment feature, each pivotally coupled to the base member, wherein the first and second attachment features each comprise an elongate member extending between the central portion and the distal portion of the base member; and a translation unit configured to engage the proximal portion of the base member and translate relative to the coupling unit, wherein the translation unit comprises:

a shaft having an external thread and extending between a proximal end and a distal end, a drive nut coupled to the proximal end of the shaft, a foot having a pusher member coupled to the distal end of the shaft and configured to engage the spinal rod, a ring with internal threading and engaging with the external threads of the shaft; and wherein the foot includes a cylindrical body that is coupled to the shaft and fixed longitudinally to the shaft but freely rotatable relative to each other.

14. The system of claim 13, wherein the distal portion of the base member comprises a pair of anchor coupling arms extending distally from the base member and separated by a channel to form the cavity.

15. The system of claim 13, wherein the base member of the coupling unit comprises:

a first longitudinal recess and a second longitudinal recess that each extend between the central portion and the distal portion of the base member, wherein the first and the second longitudinal recesses are disposed circumferentially opposite one another, and are configured to receive the first and second attachment features therein, respectively; and a first lateral recess and a second lateral recess in the central portion, wherein the first and the second lateral recesses are circumferentially opposite one another, and are configured to receive a proximal end of the first attachment feature and a proximal end of the second attachment feature therein, respectively.

16. The system of claim 15, wherein the coupling unit further comprises a first spring and a second spring disposed within the first and second lateral recesses, respectively, wherein the first and second springs are configured to engage the proximal ends of the first and second attachment features, respectively, to bias the first and second attachment features into a closed position.

17. The system of claim 13, wherein the coupling unit further comprises:

a first guide pin and a second guide pin disposed within the first and second lateral recesses, respectively, and extending into the lumen, wherein the first and second guide pins are configured to engage the translation unit to limit rotation of the pusher member relative to the shaft; and a first pivot pin and a second pivot pin disposed within the first and second longitudinal recesses, respectively, wherein the first and second attachment features are configured to pivot about the first and second pivot pins, respectively.

18. The system of claim 13, wherein each elongate member of the first and second attachment features comprises a distal end configured to engage the fixation anchor, wherein each distal end comprises a distal ridge having a tapered surface configured to pivot the distal end of the respective attachment feature outward as the fixation anchor advances into the cavity.

19. The system of claim 13, wherein the pusher member comprises:

a distal end having a pair of reduction arms configured to engage the spinal rod; and a pair of guide slots extending proximally from the pair of reduction arms, wherein the guide slots are configured to engage the coupling unit to limit rotation of the pusher member when the shaft rotates, wherein the external thread of the shaft is configured to threadably engage an internal thread on the proximal portion of the base member thereby causing the shaft to rotate and translate the translation unit relative to the coupling unit.

20. The system of claim 13, further comprising a locking cap configured to engage the fixation anchor to lock the spinal rod within the rod-capturing portion of the fixation anchor, wherein the translation unit comprises a passage extending therethrough that is dimensioned to receive the locking cap therein.

* * * * *